United States Patent
Hamaoka et al.

(10) Patent No.: US 10,478,122 B2
(45) Date of Patent: Nov. 19, 2019

(54) MEASUREMENT METHOD AND MEASUREMENT DEVICE FOR BROWN ADIPOSE TISSUE

(71) Applicants: TOKYO MEDICAL UNIVERSITY, Shinjuku-ku, Tokyo (JP); HAMAMATSU PHOTONICS K.K., Hamamatsu-shi, Shizuoka (JP)

(72) Inventors: Takafumi Hamaoka, Tokyo (JP); Shinsuke Nirengi, Kyoto (JP); Masayuki Saito, Hokkaido (JP); Takeshi Yoneshiro, Hokkaido (JP)

(73) Assignees: TOKYO MEDICAL UNIVERSITY, Shinjuku-ku, Tokyo (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 667 days.

(21) Appl. No.: 14/917,581

(22) PCT Filed: Aug. 27, 2014

(86) PCT No.: PCT/JP2014/072497
§ 371 (c)(1),
(2) Date: Mar. 9, 2016

(87) PCT Pub. No.: WO2015/037446
PCT Pub. Date: Mar. 19, 2015

(65) Prior Publication Data
US 2016/0220183 A1 Aug. 4, 2016

(30) Foreign Application Priority Data

Sep. 12, 2013 (JP) .................................. 2013-189632
Jan. 17, 2014 (JP) .................................. 2014-006914

(51) Int. Cl.
*A61B 5/00* (2006.01)
*A61B 5/1455* (2006.01)
*A61B 5/145* (2006.01)

(52) U.S. Cl.
CPC .......... *A61B 5/4872* (2013.01); *A61B 5/1455* (2013.01); *A61B 5/14546* (2013.01); *A61B 5/14551* (2013.01); *A61B 5/7275* (2013.01)

(58) Field of Classification Search
CPC . A61B 5/4872; A61B 5/7275; A61B 5/14551; A61B 5/14546; A61B 5/145
See application file for complete search history.

(56) References Cited

U.S. PATENT DOCUMENTS

2003/0139667 A1 * 7/2003 Hewko ................ A61B 5/0059
600/410

FOREIGN PATENT DOCUMENTS

JP       2002-516398 A    6/2002
WO    WO 2009067501 A2 *  5/2009  ............... A61B 5/01

OTHER PUBLICATIONS

Masayuki Saito et al., "Physiology and pathology of human brown adipose tissue," Journal of Clinical and Experimental Medicine (Igaku No Ayumi), Sep. 22, 2012, pp. 924-929, vol. 242, No. 12, including partial English translation.

(Continued)

*Primary Examiner* — Jacqueline Cheng
*Assistant Examiner* — Abid A Mustansir
(74) *Attorney, Agent, or Firm* — Drinker Biddle & Reath LLP

(57) ABSTRACT

A measurement method for brown adipose tissue includes a light input step of inputting near-infrared light from a light input unit into a measurement target portion, a light detection step of detecting light intensity of the near-infrared light having propagated through an interior of the measurement (Continued)

target portion by a light detection unit, and a calculation step of calculating an index value for a BAT amount from an oxygenated hemoglobin concentration or the like of the measurement target portion, which is acquired by near-infrared spectroscopy based on the detection result by the light detection unit.

7 Claims, 46 Drawing Sheets

(56) References Cited

OTHER PUBLICATIONS

Christian Cohage, Md et al., "Uptake in Supraclavicular Area Fat ("USA-Fat"): Description on $^{18}$F-FDG PET/CT," The Journal of Nuclear Medicine, Feb. 2003, pp. 170-176, vol. 44, No. 2.

Masayuki Saito et al., High Incidence of Metabolically Active Brown Adipose Tissue in Healthy Adult Humans Effect of Cold Exposure and Adiposity, Diabetes, Jul. 2009, pp. 1526-1531, vol. 58.

Takeshi Yoneshiro et al., "Age-Related Decrease in Cold-Activated Brown Adipose Tissue and Accumulation of Body Fat in Healthy Humans," Obesity, Nature Publishing Group, Sep. 2011, pp. 1755-1760, vol. 19, No. 9.

Masatsugu Niwayama et al., Quantitative measurement of muscle hemoglobin oxygenation using near-infrared spectroscopy with correction for the influence of a subcutaneous fat layer, Review of Scientific Instruments, American Institute of Physics, Dec. 2000, pp. 4571-4575, vol. 71, No. 12.

Otto Muzik et al., "$^{15}$PET Measurement of Blood Flow and Oxygen Consumption in Cold-Activated Human Brown Fat," Human Brown Fat Oxygen Consumption the Journal of Nuclear Medicine, Apr. 2013, pp. 523-531, vol. 54, No. 4.

Bertrand Beauvoit et al., "Time-Resolved Spectroscopy of mitochondria, cells and tissues under normal and pathological conditions," Molecular and Cellular Biochemistry, Jul. 1998, pp. 445-455, vol. 184, Nos. 1 & 2.

Atsushi Ozaki et al, "Temperature Measurement of Brown Adipose Cells Using Near-Infrared Spectroscopy," The Japan Society of Mechanical Engineers Thermal Engineering Conference 2007, 2007, pp. 393-394, including English translation.

International Preliminary Report on Patentability dated Mar. 15, 2016 for PCT/JP2014/072497.

* cited by examiner

Fig.19
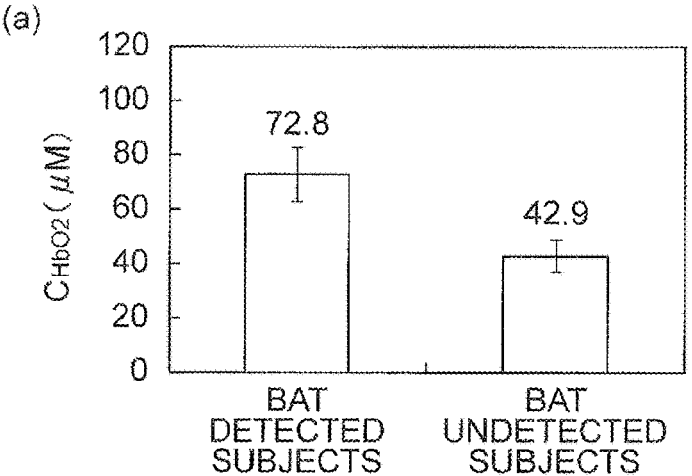
(a)
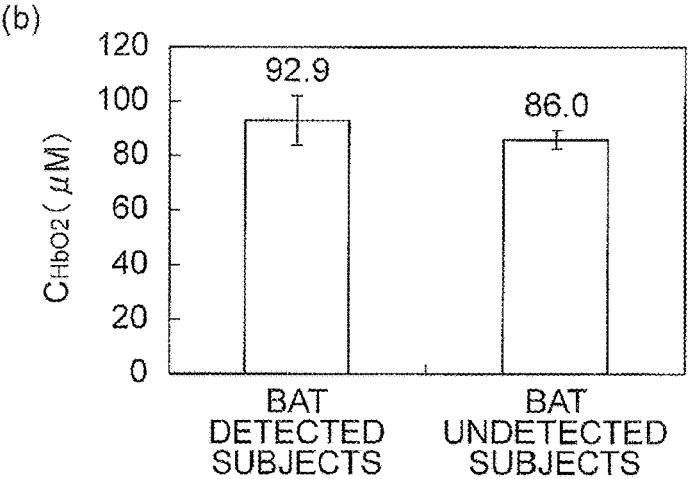
(b)
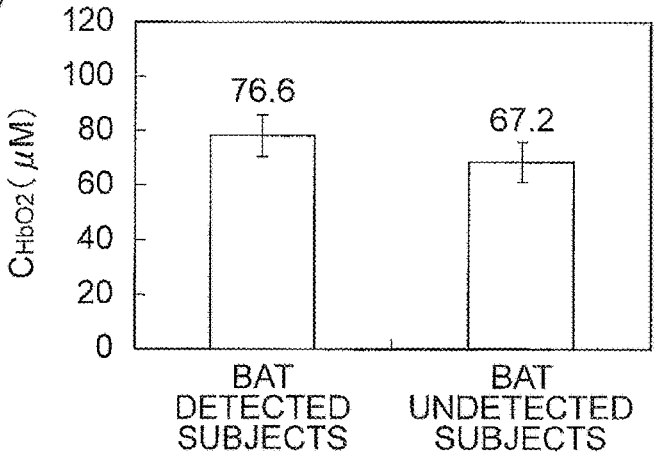
(c)

Fig.43
(a)
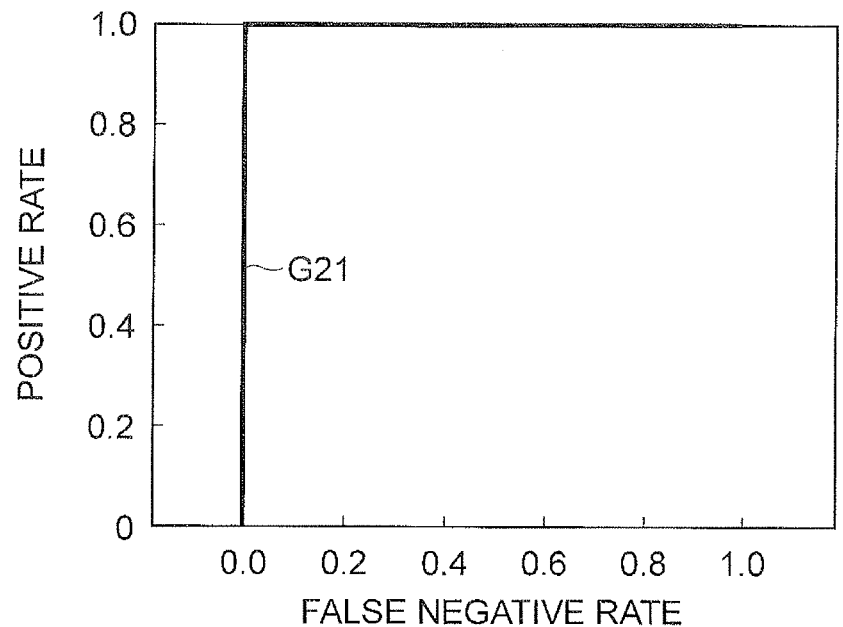
(b)
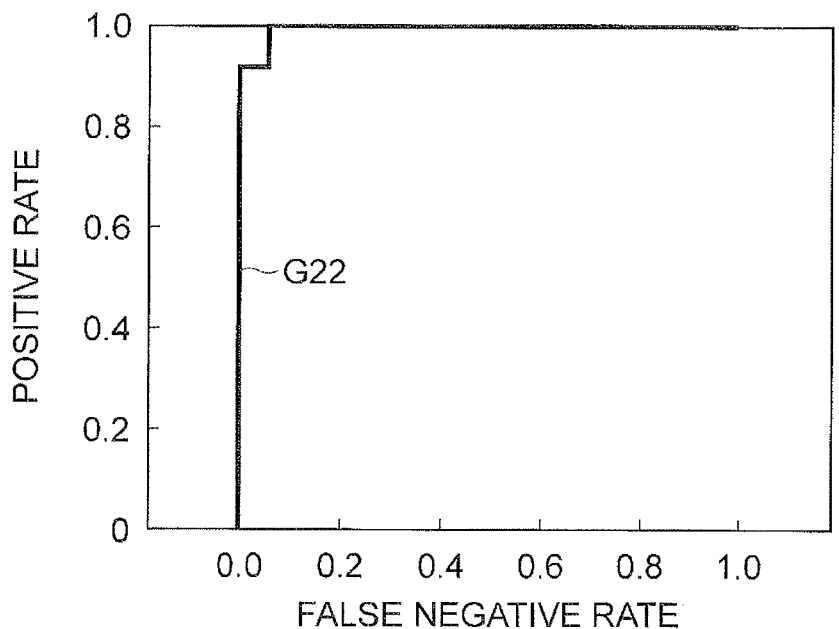

Fig.44
(a)
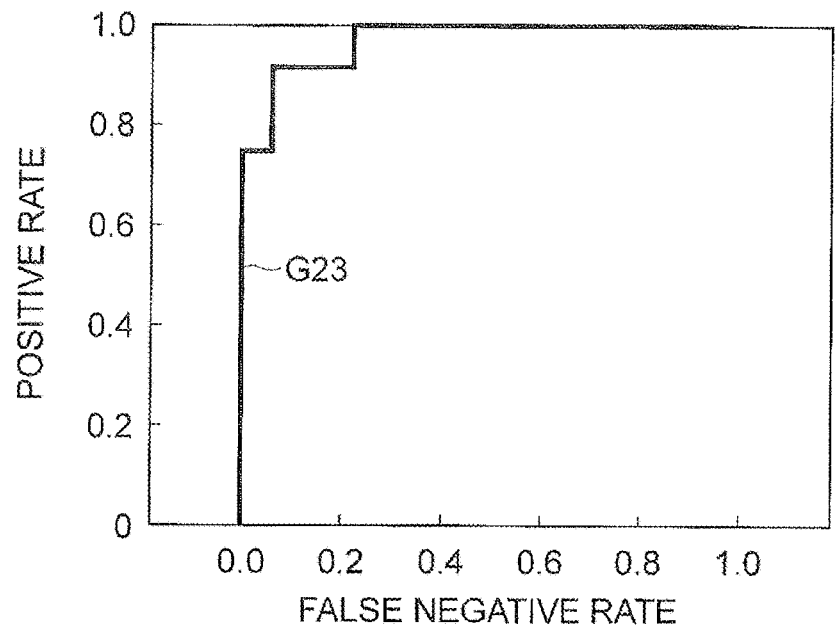
(b)
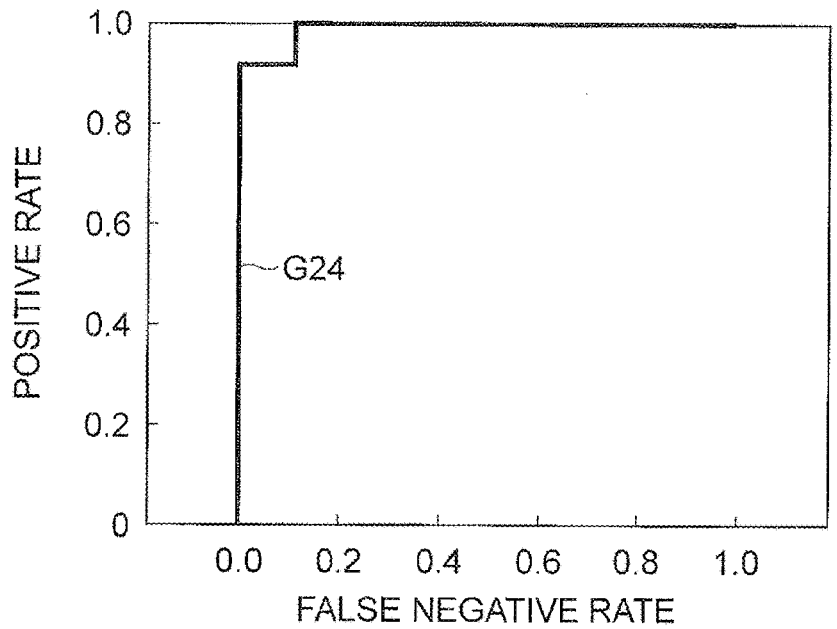

Fig.45
(a)
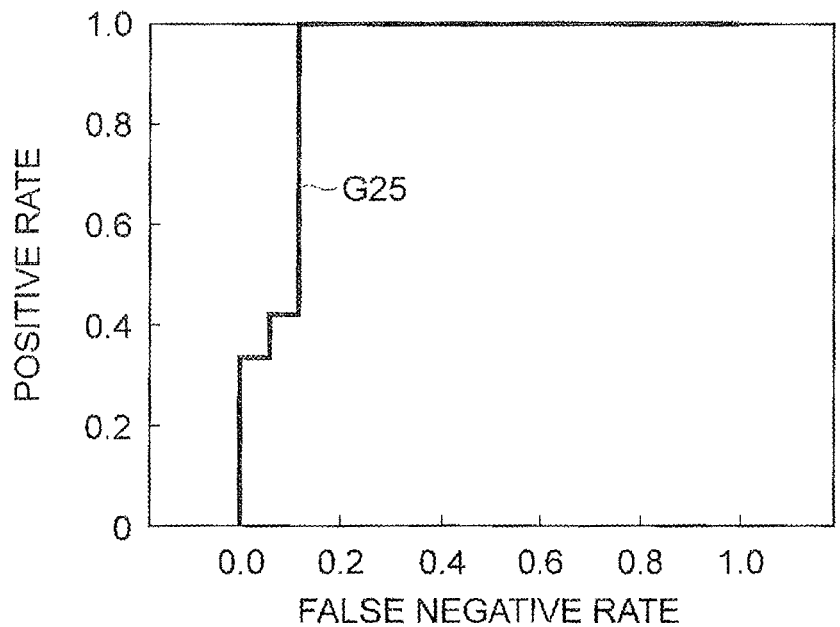
(b)
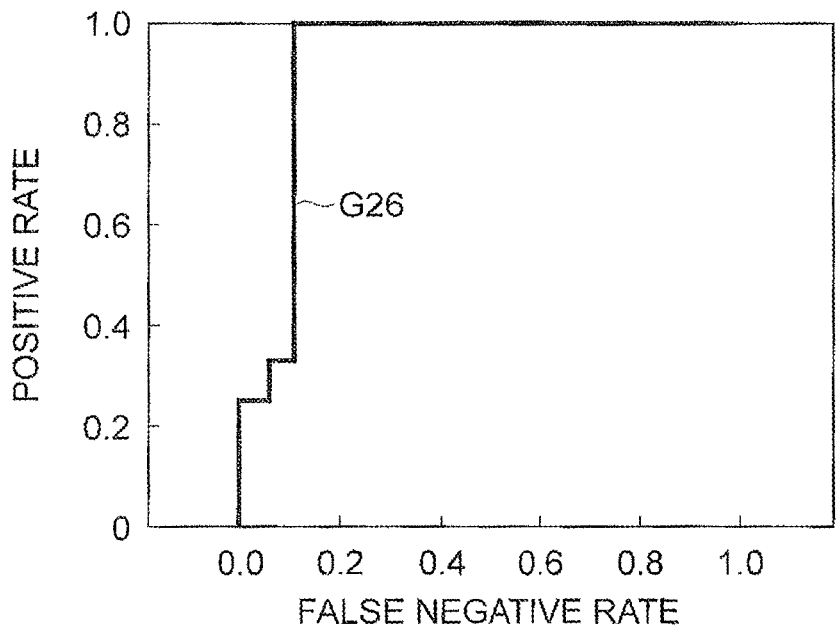

*Fig.46*
(a)
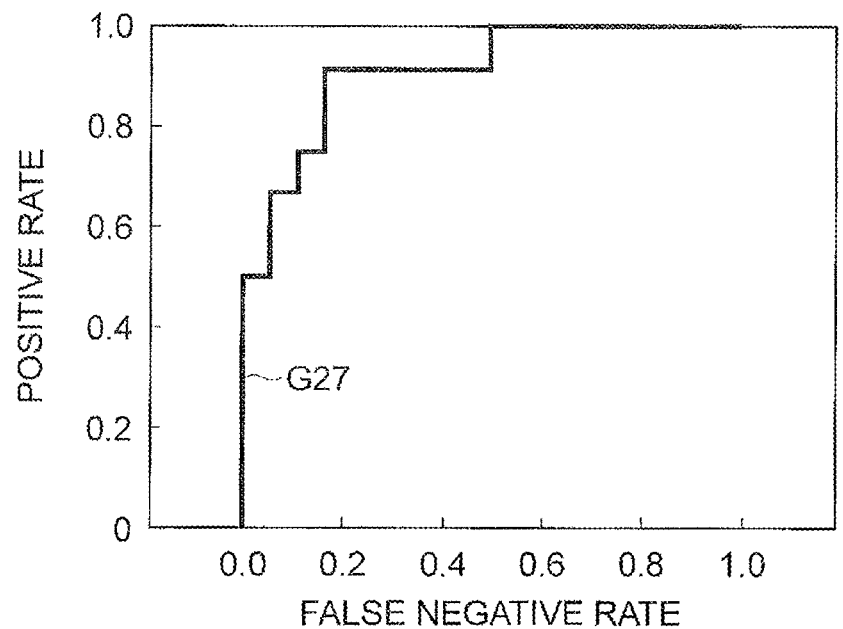
(b)
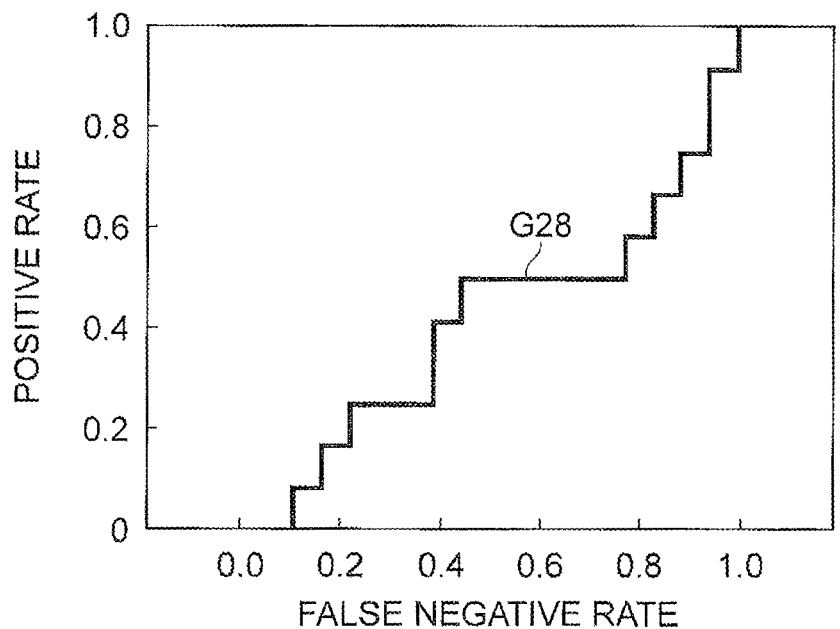

US 10,478,122 B2

MEASUREMENT METHOD AND MEASUREMENT DEVICE FOR BROWN ADIPOSE TISSUE

TECHNICAL FIELD

The present invention relates to a measurement method and a measurement apparatus for brown adipose tissue.

BACKGROUND ART

Non Patent Literature 1 describes a method for measuring the temperature of brown adipose cells, as application of a non-contact temperature measurement method by near-infrared spectroscopy for an object of a small amount of aqueous solution. In the method described in this Literature, the brown adipose cells are irradiated with infrared light and the temperature of the brown adipose cells is measured based on the absorbance thereof. Specifically, by making use of the fact that the absorption spectrum of water molecules varies depending upon temperature, noradrenaline is added to cultured. BAT cells on a laboratory dish to activate them and changes in temperature of the brown adipose cells are measured.

CITATION LIST

Non Patent Literature

Non Patent Literature 1: Atsushi Ozaki et al., "Temperature Measurement of Brown Adipose Cells Using Near-Infrared Spectroscopy," Proceedings of Thermal Engineering Conference 2007 of JSME, The Japan Society of Mechanical Engineers, pp. 393-394
Non Patent Literature 2: Masayuki Saito and Takeshi Yoneshiro, "Physiology and pathology of human brown adipose tissue," IGAKU NO AYUMI (Journal of Clinical and Experimental Medicine), Ishiyaku Publishers, Inc., September 2012, Vol. 242, No. 12, pp. 924-929
Non Patent Literature 3: Christian Cohade et al., "Uptake in Supraclavicular Area Fat ("USA-Fat"): Description on 18F-FDG PET/CT," The Journal of Nuclear Medicine, Volume 44, No. 2, February 2003, pp. 170-176
Non Patent Literature 4: Masayuki Saito et al., "High Incidence of Metabolically Active Brown Adipose Tissue in Healthy Adult Humans Effects of Cold Exposure and Adiposity," diabetes, American Diabetes Association, Volume 58, July 2009, pp. 1526-1531
Non Patent Literature 5: Takeshi Yoneshiro et al., "Age-Related Decrease in Cold-Activated Brown Adipose Tissue and Accumulation of Body Fat in Healthy Humans," Obesity, Volume 19, Number 9, pp. 1755-1760, September 2011
Non Patent Literature 6: Masatsugu Niwayama et al., "Quantitative measurement of muscle hemoglobin oxygenation using near-infrared spectroscopy with correction for the influence of a subcutaneous fat layer," Review of Scientific Instruments, American Institute of Physics, Volume 71, Number 12, pp. 4571-4575, December 2000
Non Patent Literature 7: Otto Muzik et al., "15O PET Measurement of Blood Flow and Oxygen Consumption in Cold-Activated Human Brown Fat," The Journal of Nuclear Medicine, Vol. 54, No. 4. April 2013, pp. 523-531
Non Patent Literature 8: Bertrand Beauvoit and Britton Chance, "Time-Resolved Spectroscopy of mitochondria, cells and tissues under normal and pathological conditions," Molecular and Cellular Biochemistry, 184, pp. 445-455, 1998

SUMMARY OF INVENTION

Technical Problem

There are two types of fat, "White Adipose Tissue (WAT)" which stores fat and "Brown Adipose Tissue (BAT)" which burns fat to generate heat in low-temperature environments, after eating, and so on. WAT exists throughout the entire body, whereas BAT exists in limited regions such as areas around the supraclavicular fossae, paraspinal regions, and heart. BAT loses energy in the form of heat by uncoupling protein (UCP-1) under frigidity to easily expend energy and thus is associated with prevention of adiposity and lifestyle diseases.

The conventional knowledge about BAT was mainly based on reports by animal testing. The reason for it is that it has been believed heretofore that human BAT exists in large amount in newborns but mostly disappears before adulthood, so as to have no physiological significance. However, the Inventors discovered that the activity of BAT could be evaluated by measuring tissue accumulations of fluorodeoxyglucose (FDG) by a PET (Positron Emission Tomography) apparatus and that there were adult humans with active BAT.

The Inventors conducted measurement by FDG-PET/CT for subjects of healthy adult humans after two-hours application of cold stimulation (by cooling the soles of feet by an ice bag in a room at room temperature of 19 degrees), and had the result that FDG accumulation was clearly confirmed in adipose tissue around the supraclavicular areas and thoracic vertebra. In addition, even in the case of the same subject, no FDG accumulation was confirmed without application of cold stimulation, whereby it was found that adult humans also had BAT that could be activated by cold stimulation. Furthermore, the Inventors found out that adiposity with age (middle-age spread) was caused by decrease in BAT and discovered that even functionally-declined BAT could be reactivated or increased by continuation of active cold stimulation, which would decrease body fat.

However, the foregoing method by FDG-PET/CT necessitates activation of BAT by applying the long-term cold load to the subject. In addition, the subject needs to be kept at rest for one hour or so after injection of FDG and before image acquisition, and further, the subject is exposed to radiation. As described above, the foregoing method by FDG-PET/CT imposes a great burden on the subject.

The present invention has been made in view of the problem as described above, and an object thereof is to provide a measurement method and a measurement apparatus for brown adipose tissue capable of reducing the burden on the subject.

Solution to Problem

In order to solve the above-described problem, a measurement method for brown adipose tissue according to the present invention comprises a light input step of inputting near-infrared light from a light input unit into a measurement target portion; a light detection step of detecting light intensity of the near-infrared light having propagated through an interior of the measurement target portion by a light detection unit; and a calculation step of calculating an index value for a brown adipose tissue amount from at least one value of an oxygenated hemoglobin concentration, a total hemoglobin concentration, and a first parameter of the measurement target portion, the first parameter increasing or decreasing depending upon the oxygenated hemoglobin concentration or the total hemoglobin concentration, which are acquired by near-infrared spectroscopy based on the detection result by the light detection unit.

Another measurement method for brown adipose tissue comprises a light input step of inputting near-infrared light from a light input unit into a measurement target portion; a light detection step of detecting light intensity of the near-infrared light having propagated through an interior of the measurement target portion by a light detection unit; and a calculation step of calculating an index value for a brown adipose tissue amount from at least one of a scattering coefficient and a deoxygenated hemoglobin concentration of the measurement target portion, which are acquired by near-infrared spectroscopy based on the detection result by the light detection unit.

A measurement apparatus for brown adipose tissue according to the present invention comprises a light input unit inputting near-infrared light into a measurement target portion; a light detection unit detecting light intensity of the near-infrared light having propagated through an interior of the measurement target portion; and a calculation unit calculating an index value for a brown adipose tissue amount from at least one value of an oxygenated hemoglobin concentration, a total hemoglobin concentration, and a first parameter of the measurement target portion, the first parameter increasing or decreasing depending upon the oxygenated hemoglobin concentration or the total hemoglobin concentration, which are acquired by near-infrared spectroscopy based on the detection result by the light detection unit.

Another measurement apparatus for brown adipose tissue comprises a light input unit inputting near-infrared light into a measurement target portion; a light detection unit detecting light intensity of the near-infrared light having propagated through an interior of the measurement target portion; and a calculation unit calculating an index value for a brown adipose tissue amount from at least one of a scattering coefficient and a deoxygenated hemoglobin concentration of the measurement target portion, which are acquired by near-infrared spectroscopy based on the detection result by the light detection unit.

The Inventors found out after research that there were significant correlations of the BAT amount with the oxygenated hemoglobin concentration and the total hemoglobin concentration and with the scattering coefficient and the deoxygenated hemoglobin concentration. In the foregoing measurement methods and measurement apparatuses, the calculation step (calculation unit) is configured to calculate the index value for the BAT amount, based on at least one value of the oxygenated hemoglobin concentration, the total hemoglobin concentration, and the first parameter (e.g., the absorption coefficient or the like) increasing and decreasing depending upon the oxygenated hemoglobin concentration or the total hemoglobin concentration (which will be referred to hereinafter as the hemoglobin concentration or the like), or, based on at least one of the scattering coefficient and the deoxygenated hemoglobin concentration, which are acquired by near-infrared spectroscopy. As the measurement is carried out in a non-invasive manner by use of the near-infrared spectroscopy in this way, there is no need for application of the cold load, the measurement can be done under ordinary temperature in short time (e.g., five minutes), and the subject is not exposed to radiation. Therefore, the foregoing methods and apparatuses can reduce the burden of the subject.

In general the PET apparatus is expensive and large in scale. In contrast to it, the near-infrared spectrometric apparatus is less expensive and smaller in scale than the PET apparatus. Therefore, the above methods and apparatuses can extremely simply perform the measurement of BAT.

Advantageous Effects of Invention

The measurement method and the measurement apparatus for brown adipose tissue according to the present invention have enabled reduction in burden of the subject.

BRIEF DESCRIPTION OF DRAWINGS

FIG. 19 includes graphs showing averages of corrected oxygenated hemoglobin concentrations (a) in the supraclavicular fossae, (b) in the infraclavicular areas, and (c) in the deltoid muscles.

FIG. 43 includes (a) an ROC curve of the determination result based on the index value calculated from the oxygenated hemoglobin concentration $C_{HbO2}$, and (b) an ROC curve of the determination result based on the index value calculated from the total hemoglobin concentration $C_{tHb}$.

FIG. 44 includes (a) an ROC curve of the determination result based on the index value calculated from the absorption coefficient $\mu_a$ (wavelength of 760 nm), and (b) an ROC curve of the determination result based on the index value calculated from the absorption coefficient $\mu_a$ (wavelength of 800 nm).

FIG. 45 includes (a) an ROC curve of the determination result based on the index value calculated from the scattering coefficient $\mu'_s$ (wavelength of 760 nm), and (b) an ROC curve of the determination result based on the index value calculated from the scattering coefficient $\mu'_s$ (wavelength of 800 nm).

FIG. 46 includes (a) an ROC curve of the determination result based on the index value calculated from the deoxygenated hemoglobin concentration $C_{Hb}$, and (b) an ROC curve of the determination result based on the index value calculated from the oxygen saturation $SO_2$.

DESCRIPTION OF EMBODIMENTS

Embodiments of the measurement method and the measurement apparatus according to the present invention will be described below in detail with reference to the accompanying drawings. In the description of the drawings, the same elements will be denoted by the same reference signs, without redundant description.

First Embodiment

Figure 1:
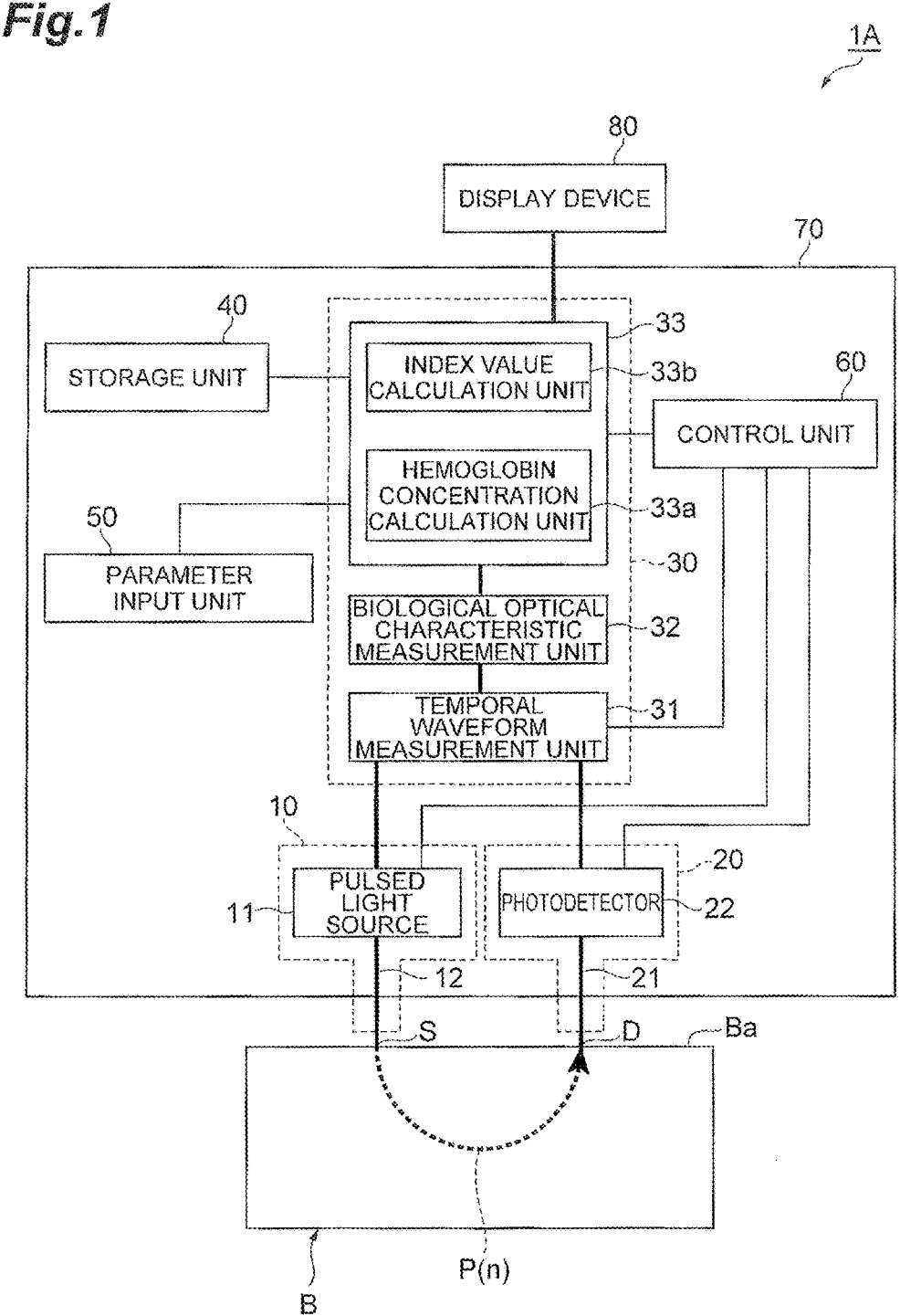
FIG. 1 is a block diagram schematically showing a configuration of one embodiment of the measurement apparatus.

FIG. 1 is a block diagram schematically showing a configuration of the first embodiment of the measurement apparatus according to the present invention. This measurement apparatus 1A is an apparatus that calculates an index value for a BAT amount from a value on a hemoglobin concentration in a measurement target portion B of a living body acquired by time-resolved spectroscopy using near-infrared light. Measurement by the measurement apparatus 1A is carried out under room temperature (constant temperature) and with the subject at rest.

The value on the hemoglobin concentration herein refers to at least one value of an oxygenated hemoglobin concentration, a total hemoglobin concentration, and, a parameter increasing or decreasing depending upon the oxygenated hemoglobin concentration or the total hemoglobin concentration. An example of the parameter increasing or decreasing depending upon the oxygenated hemoglobin concentration or the total hemoglobin concentration is a parameter (such as an absorption coefficient) used in calculating the oxygenated hemoglobin concentration or the total hemoglobin concentration. An example of the measurement target portion B is any portion of the living body. For example, it may be the supraclavicular fossa, the paraspinal area, and the area around the heart where BAT exists in large amount.

The measurement apparatus 1A shown in FIG. 1 has a main body section 70 and a display device 80. The main body section 70 has a light input unit 10, a light detection unit 20, a calculation unit 30, a parameter input unit 50, and a control unit 60 to control these units.

The light input unit 10 inputs near-infrared pulsed light beams P(n) (where n=1, 2, . . . ) of wavelengths different from each other, from a light input position S of the measurement target portion B. In the present embodiment, the light input position S is set at one location on a surface Ba of the measurement target portion B. The light input unit 10 includes a pulsed light source 11 to generate the pulsed light beams P(n), and a light input light guide 12. An input end of the light input light guide 12 is optically coupled to the pulsed light source 11. An output end of the light input light guide 12 is located at the light input position. S of the measurement target portion B.

The pulsed light source 11 to be used herein can be selected from various light sources such as light emitting diodes, laser diodes, and various pulsed laser devices. The pulsed light beams P(n) generated by the pulsed light source 11 to be used herein can be near-infrared pulsed light beams durations of pulses of which are short enough to measure changes in absorption coefficient of the measurement target portion B and center wavelengths of which are wavelengths where the light absorptance is high in light absorption characteristic of a measurement target material. In an example, n=3 and the wavelengths of the pulsed light beams P(1) to P(3) are 760 nm, 795 nm, and 830 nm, respectively. The light input light guide 12 to be used herein can be, for example, an optical fiber.

The light detection unit 20 detects the pulsed light beams P(n) having propagated through the interior of the measurement target portion B, as detected light. In the present embodiment, a light detection position D is set at one location on the surface Ba of the measurement target portion B. The light detection unit 20 includes a light detection light guide 21, and a photodetector 22 to detect light and convert the light into an electric detection signal. An input end of the light detection light guide 21 is located at the light detection position D of the measurement target portion B. An output end of the light detection light guide 21 is optically coupled to the photodetector 22.

The light detection light guide 21 to be used herein can be, for example, an optical fiber. The photodetector 22 to be used herein can be selected from various devices such as photomultiplier tubes, photodiodes, avalanche photodiodes, and PIN photodiodes. The selection of the photodetector 22 needs only to satisfy the condition that the detector has a spectral sensitivity characteristic enough to satisfactorily detect light intensity in the wavelength range of the pulsed light beams P(n) output from the pulsed light source 11. If the detected light is weak, the photodetector with high sensitivity or with a high gain may be used.

Figure 2:
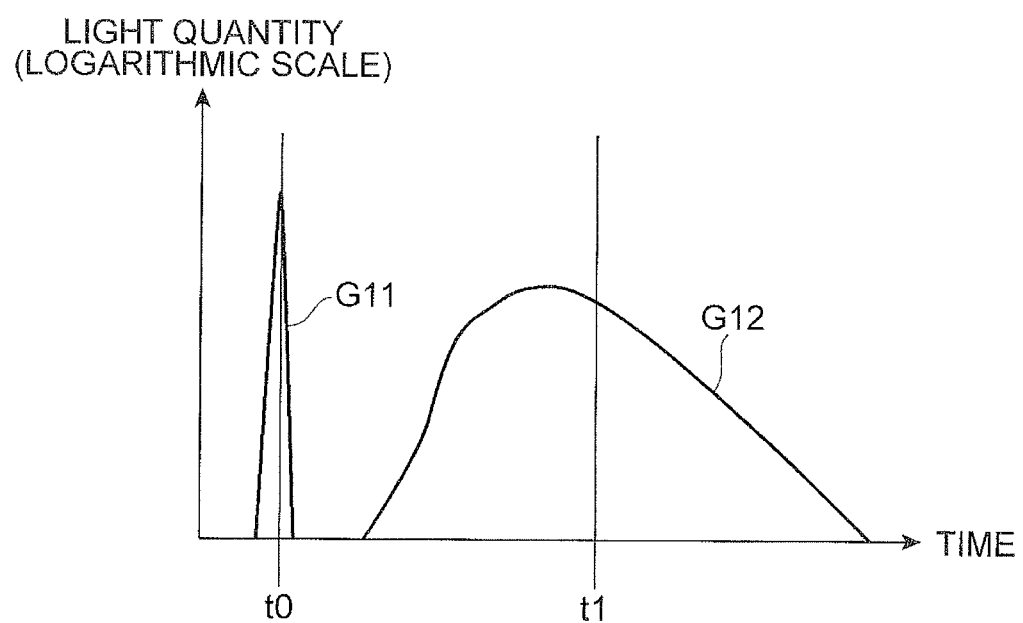
FIG. 2 is a graph showing an example of temporal changes in light intensity of pulsed light output from a light input unit and in light intensity of detected light detected by a light detection unit.

FIG. 2 is a graph showing an example of temporal changes in light intensity of the pulsed light P(n) output from the light input unit 10 and light intensity of the detected light detected by the light detection unit 20. In FIG. 2, the vertical axis represents the light quantity (in logarithmic scale) and the horizontal axis the time. Graph G11 is a temporal waveform (input waveform) of intensity of the pulsed light input at a time $t_0$ from the light input unit 10 into the measurement target portion B. Graph G12 is a temporal waveform (detected waveform) of intensity of the detected light corresponding to the pulsed light input at the time $t_0$. The time when the light having propagated through the interior of the measurement target portion B arrives at the light detection position D is different depending upon propagation circumstances of the light, and the light is attenuated by scattering and absorption in the measurement target portion. B. Therefore, the detected waveform is a certain distribution curve, as shown by Graph G12 in FIG. 2.

Reference is made again to FIG. 1. The calculation unit 30 includes a temporal waveform measurement unit 31, a biological optical characteristic measurement unit 32, and a calculation processing unit 33. The temporal waveform measurement unit 31 is electrically coupled to the photodetector 22 and acquires the temporal waveform of light intensity of the detected light based on the light detection signal from the photodetector 22. For acquiring this temporal waveform, a trigger signal indicating emission timing of the pulsed light P(n) is supplied from the pulsed light source 11 to the temporal waveform measurement unit 31. The input and detection of the pulsed light P(n) are carried out at the plurality of measurement times, thereby acquiring the temporal waveforms at the respective measurement times. The biological optical characteristic measurement unit 32 calculates a parameter (e.g., an absorption coefficient) indicating a light absorption characteristic of the measurement target portion B, based on the temporal waveforms acquired by the temporal waveform measurement unit 31.

The calculation processing unit 33 includes a hemoglobin concentration calculation unit 33a and an index value calculation unit 33b. The hemoglobin concentration calculation unit 33a acquires the parameter indicating the light absorption characteristic of the measurement target portion B from the biological optical characteristic measurement unit 32 and performs a predetermined calculation operation to calculate various hemoglobin concentrations (including at least one of the oxygenated hemoglobin concentration and the total hemoglobin concentration) in the measurement target portion B. The index value calculation unit 33b calculates the index value for the BAT amount from at least one value of the oxygenated hemoglobin concentration and the total hemoglobin concentration calculated by the hemoglobin concentration calculation unit 33a and the parameter (e.g., the absorption coefficient) increasing or decreasing depending upon the oxygenated hemoglobin concentration or the total hemoglobin concentration, calculated by the biological optical characteristic measurement unit 32.

The display device 80 is connected to the main body section 70. The display device 80 displays the index value for the BAT amount calculated by the index value calculation unit 33b of the calculation processing unit 33, to provide the index value to a person performing measurement and a subject.

The following will detail an example of the calculation contents in the biological optical characteristic measurement unit 32 and the calculation processing unit 33. The biological optical characteristic measurement unit 32 obtains the absorption coefficient $\mu_{a, \lambda}$ at each wavelength $\lambda$ in the measurement target portion B, based on the temporal waveform of detected light (e.g., cf. FIG. 2) provided from the temporal waveform measurement unit 31. Namely, in one example, it obtains the absorption coefficient $\mu_{a, 760}$ at the wavelength of 760 nm, the absorption coefficient $\mu_{a, 795}$ at the wavelength of 795 nm, and the absorption coefficient $\mu_{a, 830}$ at the wavelength of 830 nm. These absorption coefficients $\mu_{a, \lambda}$ are suitably obtained, for example, by use of the diffusion equation.

The hemoglobin concentration calculation unit 33a of the calculation processing unit 33 solves the system of equations for the absorption coefficients $\mu_{a, \lambda}$ represented by Formula (1) below, to calculate the oxygenated hemoglobin concentration ($C_{HbO2}$) and deoxygenated hemoglobin concentration ($C_{Hb}$) of the measurement target portion B. It is noted that $\varepsilon_{HbO2, \lambda}$ is the extinction coefficient of oxygenated hemoglobin at the wavelength λ and $\varepsilon_{Hb,\lambda}$ is the extinction coefficient of deoxygenated hemoglobin at the wavelength λ, both of which are known values. Furthermore, the hemoglobin concentration calculation unit 33a calculates the total hemoglobin concentration ($C_{tHb}$) from these hemoglobin concentrations. The hemoglobin concentration calculation unit 33a can also calculate an oxygen saturation ($SO_2$) from these hemoglobin concentrations if necessary.

[Math I]

$$\mu_{a,\lambda}=\varepsilon_{HbO2,\lambda}C_{HbO2}+\varepsilon_{Hb,\lambda}C_{Hb} \quad (1)$$

The index value calculation unit 33b of the calculation processing unit 33 calculates the index value for the BAT amount, based on the oxygenated hemoglobin concentration and/or the total hemoglobin concentration calculated by the hemoglobin concentration calculation unit 33a and a parameter for a body fat amount of the subject. The parameter for the body fat amount of the subject herein can be, for example, a body fat percentage. The parameter for the body fat amount of the subject is input from the parameter input unit 50 and is supplied to the index value calculation unit 33b.

The main body section 70 further has a storage unit 40, for example, such as a nonvolatile memory. The storage unit 40 stores in advance data indicating a correlation of the parameter for the body fat amount with the oxygenated hemoglobin concentration and/or the total hemoglobin concentration. The index value calculation unit 33b calculates, as the index value for the BAT amount, a value corrected so as to reduce influence of the body fat amount (mainly, subcutaneous fat) on the oxygenated hemoglobin concentration and/or the total hemoglobin concentration, using the correlation data stored in the storage unit 40. A method of the calculation at this time can be, for example, the univariate analysis method. Examples of methods for measuring the body fat percentage include the caliper method, the bioelectrical impedance analysis method (BIA method), the air displacement method, the underwater weighing method, the dual-energy X-ray absorptiometry method (DXA method), and so on.

Figure 3:
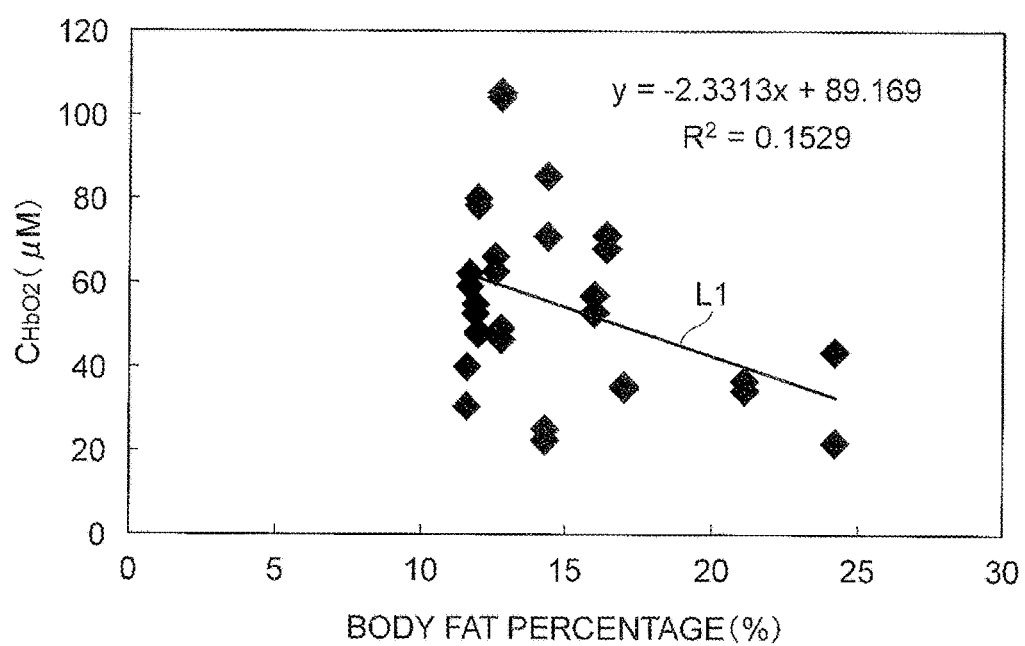
FIG. 3 is a graph showing a correlation between oxygenated hemoglobin concentration and body fat percentage in the supraclavicular fossae, as an example of correlation stored in a storage unit.

FIG. 3 is a graph showing a correlation between oxygenated hemoglobin concentration ($C_{HbO2}$) and body fat percentage in the supraclavicular fossae, as an example of the correlation stored in the storage unit 40. In FIG. 3, the vertical axis represents the oxygenated hemoglobin concentration (unit: μM) and the horizontal axis the body fat percentage (unit: %). The correlation data between oxygenated hemoglobin concentration and body fat percentage in the supraclavicular fossae is suitably represented, for example, by an approximate straight line L1 shown in FIG. 3. However, the correlation data stored in the storage unit 40 does not have to be limited to the one approximate straight line L1, and the approximate straight line may vary with increase in number of data.

In the above-described configuration, the index value calculation unit 33b calculates the index value for the BAT amount from the oxygenated hemoglobin concentration and/or the total hemoglobin concentration, but the index value calculation unit 33b may calculate the index value for the BAT amount from the parameter (e.g., the absorption coefficient $\mu_{a,\lambda}$ or the like) increasing or decreasing depending upon the oxygenated hemoglobin concentration or the total hemoglobin concentration, or may calculate the index value for the BAT amount by use of both of this parameter and the oxygenated hemoglobin concentration and/or the total hemoglobin concentration. In that case, the storage unit 40 is suitably configured so as to store in advance data indicating a correlation between the parameter for the body fat amount and the above-mentioned parameter.

Figure 4:
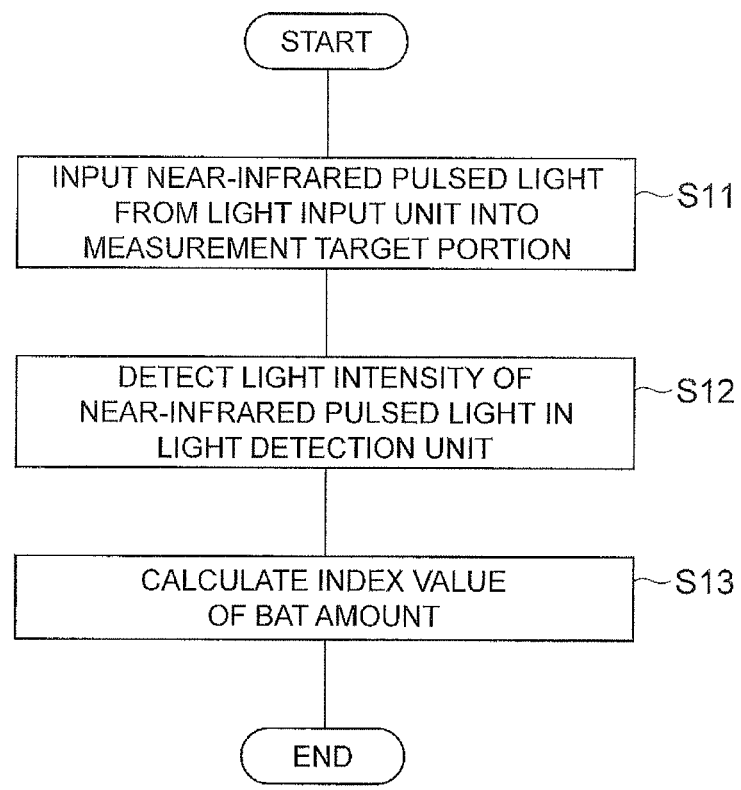
FIG. 4 is a flowchart showing a measurement method according to one embodiment.

The operation of the measurement apparatus 1A having the above configuration and one embodiment of the measurement method according to the present invention will be described. FIG. 4 is a flowchart showing the measurement method according to the present embodiment. As shown in FIG. 4, first, the near-infrared pulsed light P(n) is input from the light input unit 10 into the measurement target portion B (light input step S11). Next, the light detection unit 20 detects the light intensity of the near-infrared pulsed light P(n) having propagated through the interior of the measurement target portion B (light detection step S12).

Subsequently, by the time-resolved spectroscopy based on the detection result by the light detection unit 20, the calculation unit 30 obtains at least one value of the oxygenated hemoglobin concentration and/or the total hemoglobin concentration of the measurement target portion B, and, the parameter (e.g., the absorption coefficient $\mu_{a,\lambda}$ or the like) increasing or decreasing depending upon the oxygenated hemoglobin concentration or the total hemoglobin concentration. Then the calculation unit 30 calculates the index value for the BAT amount from this at least one value (calculation step S13). At this time, the index value for the BAT amount can be well determined to be a value corrected so as to reduce the influence of the body fat amount, using the parameter for the body fat amount input from the parameter input unit 50 and the data indicating the correlation with the foregoing at least one value, as stored in the storage unit 40.

The below will describe effects achieved by the measurement apparatus 1A and measurement method of the present embodiment with the foregoing configuration. As described above, the Inventors have discovered heretofore that the activity of BAT could be evaluated by measuring a tissue accumulation of FDG by use of the PET apparatus. However, such a method using the PET apparatus requires the subject to be kept under a cold load for a long period to activate BAT, in addition, after injection of FDG, the subject needs to be kept at rest for about one hour before image acquisition, the subject is also inevitably exposed to radiation, thus there is a great burden imposed on the subject. Furthermore, a measurable season is limited to winter.

The Inventors found out after research that there was a significant correlation of the BAT amount with the oxygenated hemoglobin concentration and the total hemoglobin concentration, as described in below-described Example. According to the Inventors' knowledge, there are a large number of blood capillaries in BAT and, when activated, an amount of blood increases so as to become larger than in WAT. Therefore, it is considered that the blood amount increases as an activity value of BAT (maximum value of FDG accumulation, $SUV_{max}$) becomes higher.

In the measurement apparatus 1A and measurement method of the present embodiment, the calculation unit 30 and calculation step S13 are configured to calculate the index value for the BAT amount, based on at least one value of the oxygenated hemoglobin concentration, the total hemoglobin concentration, and the parameter (first parameter) such as the absorption coefficient increasing or decreasing depending upon these, obtained by the time-resolved spectroscopy being a kind of near-infrared spectroscopy. As the measurement is carried out in a non-invasive manner by the near-infrared spectroscopy in this way, there is no need for application of the cold load, and the measurement can be performed under ordinary temperature in short time (e.g., five minutes). The subject does not have to be exposed to radiation. Therefore, the measurement apparatus 1A and measurement method of the present embodiment can significantly reduce the burden on the subject. Furthermore, there are no restrictions on measurable seasons. Then, spread of such simple method will allow the BAT amount to be measured without subject's burden and can advance the research on human BAT, including development, evaluation, etc. of anti-obesity methods for adult humans.

The PET apparatus is expensive and large in scale in general. In contrast to it, the near-infrared spectrometric apparatus like the measurement apparatus 1A of the present embodiment can be configured at lower cost and in smaller scale than the PET apparatus. Therefore, the measurement apparatus 1A and measurement method of the present embodiment can perform the measurement of BAT extremely simply.

Non Patent Literature 1 also uses the near-infrared spectrometric method, but Non Patent Literature 1 uses the cultured cells as measurement object and measures the temperature of the cells with focus on the temperature of water. In contrast to it, the measurement apparatus 1A and measurement method of the present embodiment are different from the method described in Non Patent Literature 1, in that the objective thereof is quantification of BAT amount, with focus on the relationship of the BAT amount with the hemoglobin concentration or the like.

As in the present embodiment, the calculation unit 30 and calculation step S13 may define, as the index value for the BAT amount, the value corrected so as to reduce the influence of the body fat amount on the hemoglobin concentration or the like, using the data indicating the correlation between the parameter (second parameter) for the body fat amount and the hemoglobin concentration or the like.

The hemoglobin concentration or the like measured by the near-infrared spectrometric method is likely to be affected by white adipose tissue (WAT) such as subcutaneous fat. Namely, the absorbance of WAT is extremely smaller than that of muscle and the WAT amount or body fat amount varies widely from individual to individual, therefore, there is a tendency such that the hemoglobin concentration is estimated lower for people with more body fat and the hemoglobin concentration is estimated higher for people with less body fat. Since BAT promotes energy expenditure, people with higher activity values of BAT tend to have less body fat. Therefore, there is a possibility that the individual difference of body fat amount is directly reflected in the value of the hemoglobin concentration or the like. In the measurement apparatus 1A and measurement method of the present embodiment, the value is corrected so as to reduce the influence of the body fat amount included in the hemoglobin concentration or the like, for example, using the data indicating the correlation between the parameter for the body fat amount such as the body fat percentage and the hemoglobin concentration or the like, and the value after correction is defined as the index value for the BAT amount. This allows the BAT amount to be evaluated more accurately, while restraining the influence of the body fat amount on the index value.

First Example

The following will describe the result of an experiment to check the correlation between BAT activity value and hemoglobin concentration or the like with a plurality of subjects, conducted by the Inventors. In this experiment, each of fifteen subjects was kept at rest in a room at ordinary temperature (27 degrees) for five minutes, without cold stimulation, and then the hemoglobin concentration in each of the left and right supraclavicular fossae as BAT neighboring portions, and the left and right infraclavicular areas and deltoid muscles as contrasting portions was measured by use of the time-resolved spectrometric apparatus. For each of the same subjects, the cold stimulation was applied (by cooling the soles of feet by an ice bag in a room at 19° C. for two hours) and thereafter the tissue accumulation of FDG was measured by use of the PET apparatus to obtain the activity of BAT ($SUV_{max}$) in the supraclavicular fossae (BAT neighborhoods).

The PET images of the fifteen subjects were classified into BAT detected subjects and BAT undetected subjects and there were six BAT detected subjects and nine BAT undetected subjects. Table 1 below is a table showing characteristics of the respective BAT detected subjects and BAT undetected subjects.

TABLE 1

| Items | BAT detected subjects | BAT undetected subjects |
|---|---|---|
| number of subjects (persons) | 6 | 9 |
| age (years) | 21.5 ± 1.4 | 25.1 ± 2.8 |
| height (cm) | 171.5 ± 3.4 | 175.2 ± 6.9 |
| weight (kg) | 60.6 ± 5.3 | 67.1 ± 7.4 |
| BMI (kg/m$^2$) | 20.6 ± 1.1 | 21.9 ± 2.1 |
| body fat percentage (%) | 13.3 ± 1.8 | 15.5 ± 4.6 |
| BAT activity value $SUV_{max}$ | 7.9 ± 5.2 | 1.5 ± 0.4 |

Figure 5:
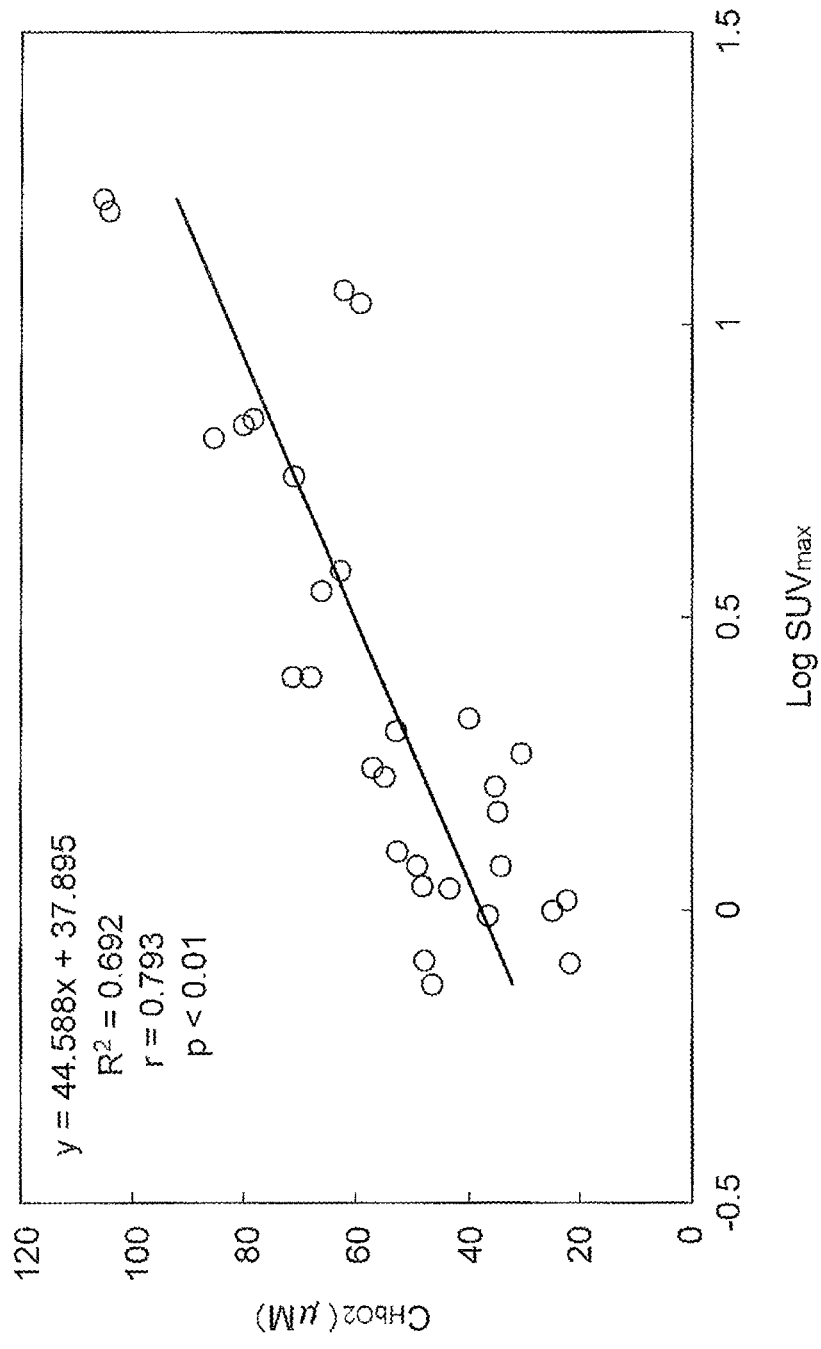
FIG. 5 is a graph showing a relation between oxygenated hemoglobin concentration and activity of BAT in the supraclavicular fossae.
Figure 6:
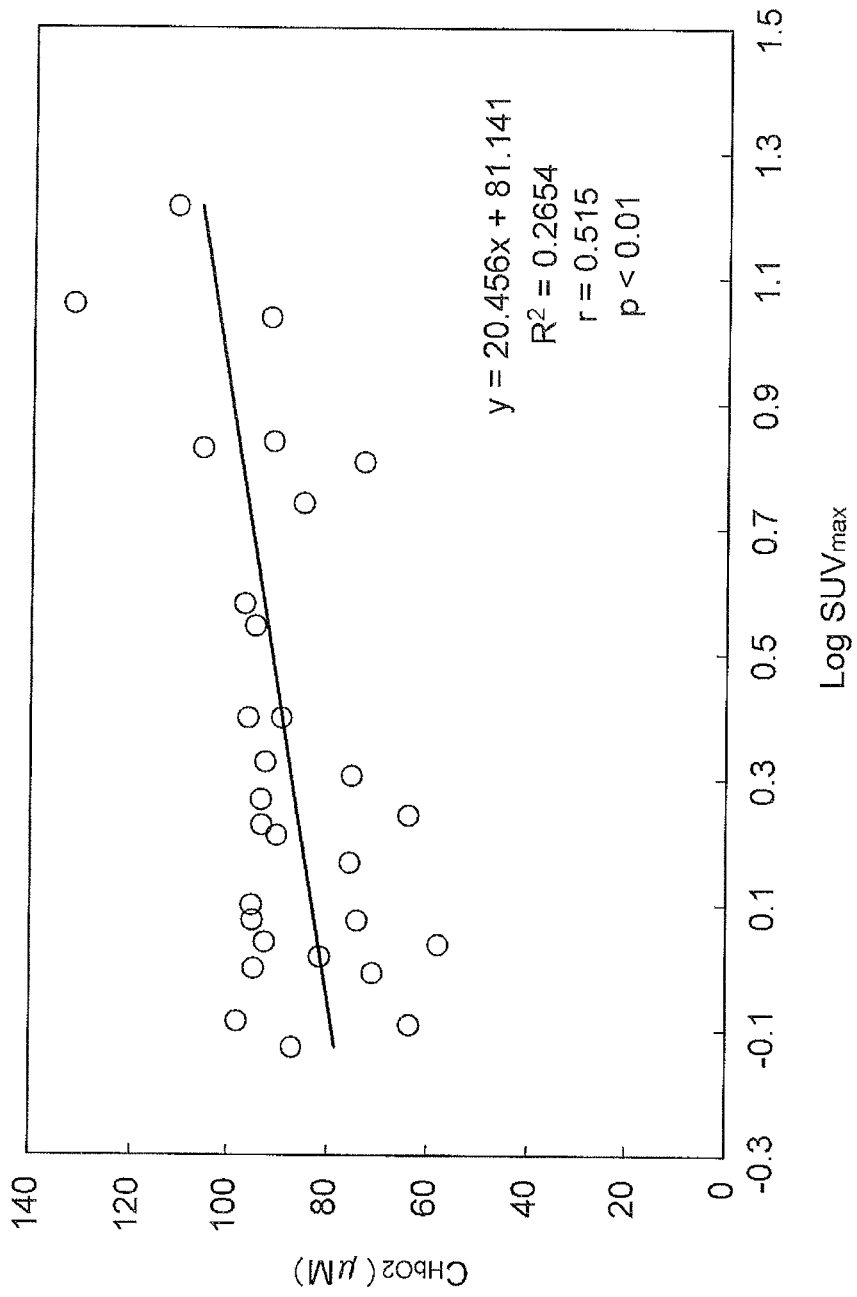
FIG. 6 is a graph showing a relation between oxygenated hemoglobin concentration and activity of BAT in the infraclavicular areas.
Figure 7:
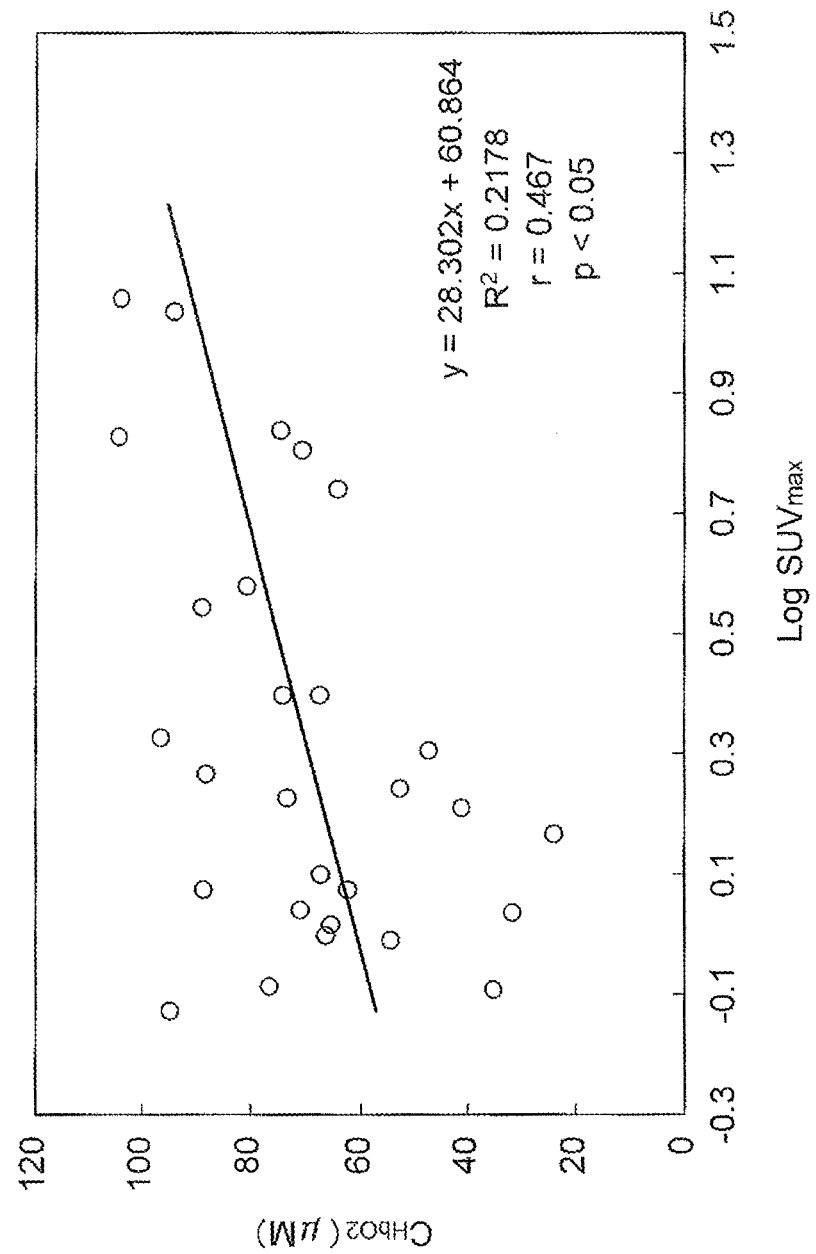
FIG. 7 is a graph showing a relation between oxygenated hemoglobin concentration and activity of BAT in the deltoid muscles.

FIG. 5 to FIG. 7 are graphs showing relations between oxygenated hemoglobin concentration $C_{HbO2}$ and BAT activity $SUV_{max}$. FIG. 5 shows the relation in the supraclavicular fossae, FIG. 6 the relation in the infraclavicular areas, and FIG. 7 the relation in the deltoid muscles. The vertical axis represents the oxygenated hemoglobin concentration $C_{HbO2}$ (unit: μM) and the horizontal axis the common logarithm of activity $SUV_{max}$. In each of FIG. 5 and subsequent figures, a relational expression including x and y is an equation indicating an approximate straight line and R represents a correlation coefficient of the approximate straight line.

As shown in FIG. 5 to FIG. 7, a certain level of correlation was found between oxygenated hemoglobin concentration and activity $SUV_{max}$ of BAT, in every measurement target portion. Namely, as the oxygenated hemoglobin concentration increases, the activity $SUV_{max}$ also becomes larger, not only in the supraclavicular fossae where BAT exists, but also in the infraclavicular areas and deltoid muscles where BAT rarely exists. However, it can be mentioned that there is a significant correlation stronger in the supraclavicular fossae where BAT exists, than in the other measurement target portions.

Figure 8:
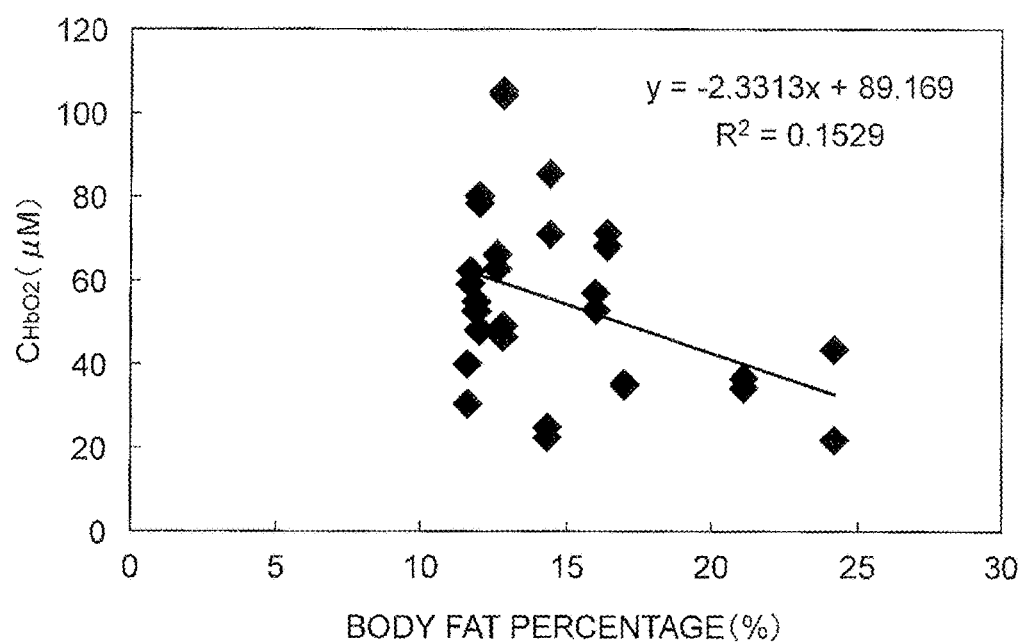
FIG. 8 is a graph showing a correlation between oxygenated hemoglobin concentration and body fat percentage in the supraclavicular fossae.
Figure 9:
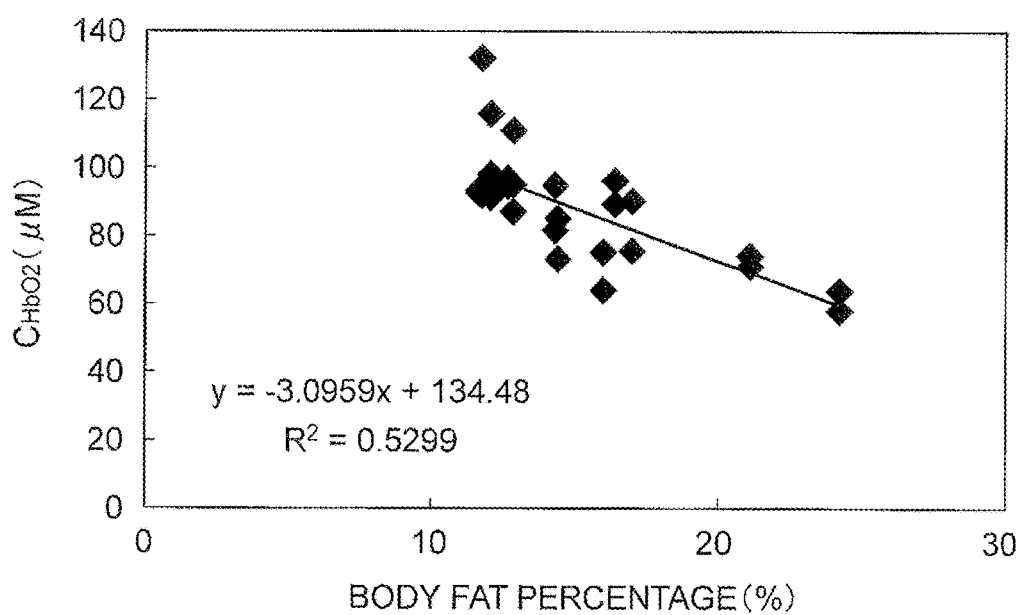
FIG. 9 is a graph showing a correlation between oxygenated hemoglobin concentration and body fat percentage in the infraclavicular areas.
Figure 10:
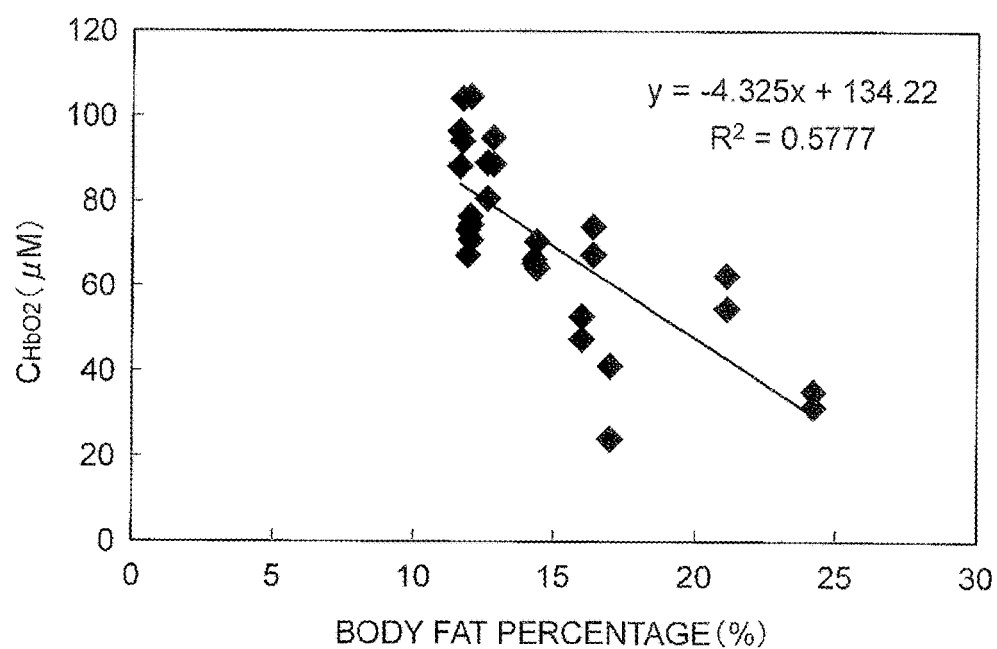
FIG. 10 is a graph showing a correlation between oxygenated hemoglobin concentration and body fat percentage in the deltoid muscles.

In the present example, the body fat percentage of each subject was measured in order to check the correlation between oxygenated hemoglobin concentration $C_{HbO2}$ and body fat percentage. FIG. 8 to FIG. 10 are graphs showing the correlations between oxygenated hemoglobin concentration $C_{HbO2}$ and body fat percentage. FIG. 8 shows the relation in the supraclavicular fossae, FIG. 9 the relation in the infraclavicular areas, and FIG. 10 the relation in the deltoid muscles. The vertical axis represents the oxygenated hemoglobin concentration $C_{HbO2}$ (unit: μM) and the horizontal axis the body fat percentage (unit: %).

As shown in FIG. 8 to FIG. 10, a certain level of correlation was found between calculated value of oxygenated hemoglobin concentration $C_{HbO2}$ and body fat percentage, in every measurement target portion. A conceivable reason for it is that the hemoglobin concentration measured by the near-infrared spectroscopy is likely to be affected by WAT, as described above. Then, in the present example, correction was made so as to reduce the influence of the body fat percentage on the oxygenated hemoglobin concentration $C_{HbO2}$, by use of a method (univariate analysis) as described below.

Figure 11:
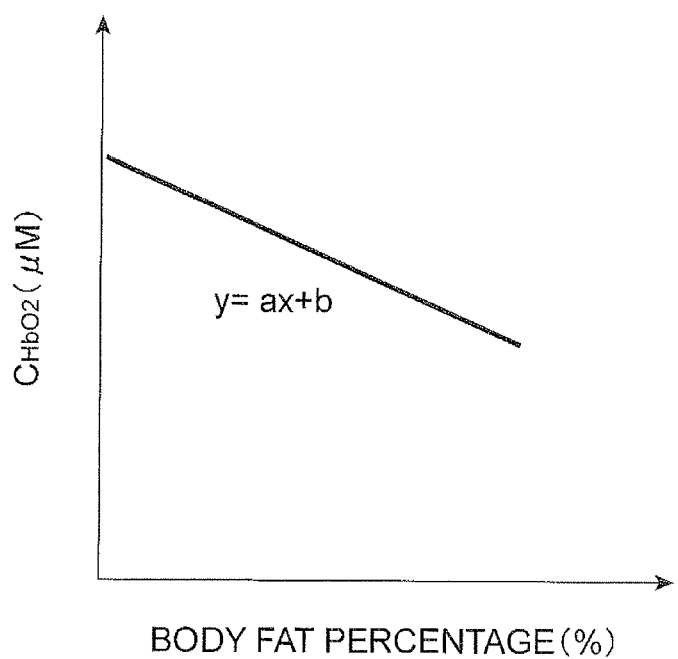
FIG. 11 is a graph showing a typical correlation between oxygenated hemoglobin concentration and body fat percentage.

FIG. 11 is a graph showing a typical correlation between oxygenated hemoglobin concentration $C_{HbO2}$ and body fat percentage. In many cases, as shown in FIG. 11, there is a linear relation between oxygenated hemoglobin concentration $C_{HbO2}$ and body fat percentage. Now, let the following expression represent a relation between body fat percentage x (%) and oxygenated hemoglobin concentration y (µM) of all the subjects.

$$y = ax + b \quad (2)$$

For example, when the body fat percentage x of a certain subject is assumed to be 15% and substituted into the above Formula (2), a theoretical value C1 of the oxygenated hemoglobin concentration of the subject is given as follows.

$$15 \times a + b = C1 \quad (3)$$

When the theoretical value C1 is subtracted from a measured value C2 of the oxygenated hemoglobin concentration of the subject, we have a difference D. This difference D corresponds to the oxygenated hemoglobin concentration obtained when the body fat percentage is 0%.

$$C2 - C1 = D \quad (4)$$

Here, by multiplying an average value $x_0$ of the body fat percentages of all the subjects by a and adding b, an average value $y_0$ of oxygenated hemoglobin concentrations is obtained.

$$y_0 = ax_0 + b \quad (5)$$

By adding the difference D of the subject to the average $y_0$, a corrected oxygenated hemoglobin concentration C3 is obtained.

$$C3 = D + y_0 = D + (ax_0 + b) \quad (6)$$

By the above calculation, the oxygenated hemoglobin concentration $C_{HbO2}$ corrected so as to reduce the influence of the body fat percentage can be obtained.

Figure 12:
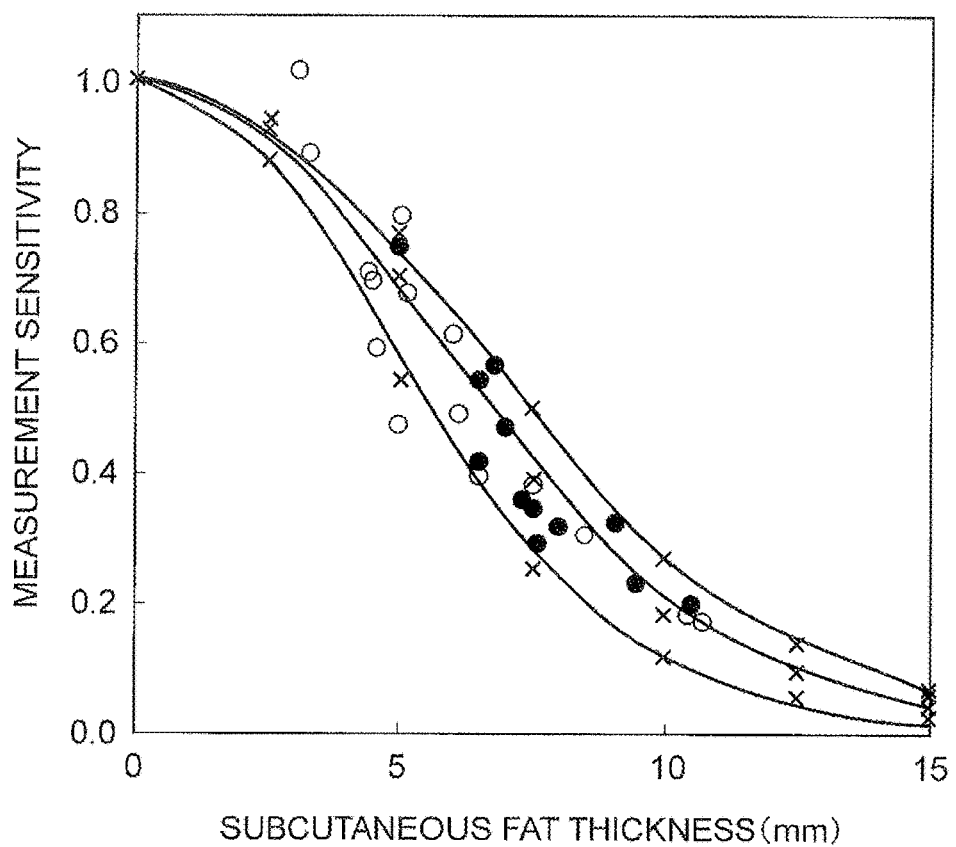
FIG. 12 is a graph showing an example of relations between subcutaneous fat thickness and measurement sensitivity.

The correction method for the hemoglobin concentration or the like does not have to be limited to the above. For example, the correction may be made using another parameter for the body fat amount, instead of the body fat percentage. Examples of other parameters include the thickness of subcutaneous fat, a fat amount estimated from a spectral characteristic, and so on. FIG. 12 is a graph showing an example of relations between subcutaneous fat thickness and measurement sensitivity, which is described in Non Patent Literature 6. The hemoglobin concentration or the like may be corrected using such relations. For example, when the measurement sensitivity at the subcutaneous fat thickness of 5 mm is 0.7, the hemoglobin concentration or the like with the subcutaneous fat of 0 mm (i.e., excluding influence of subcutaneous fat thickness) can be calculated, by dividing the measured hemoglobin concentration or the like by the measurement sensitivity 0.7.

Figure 13:
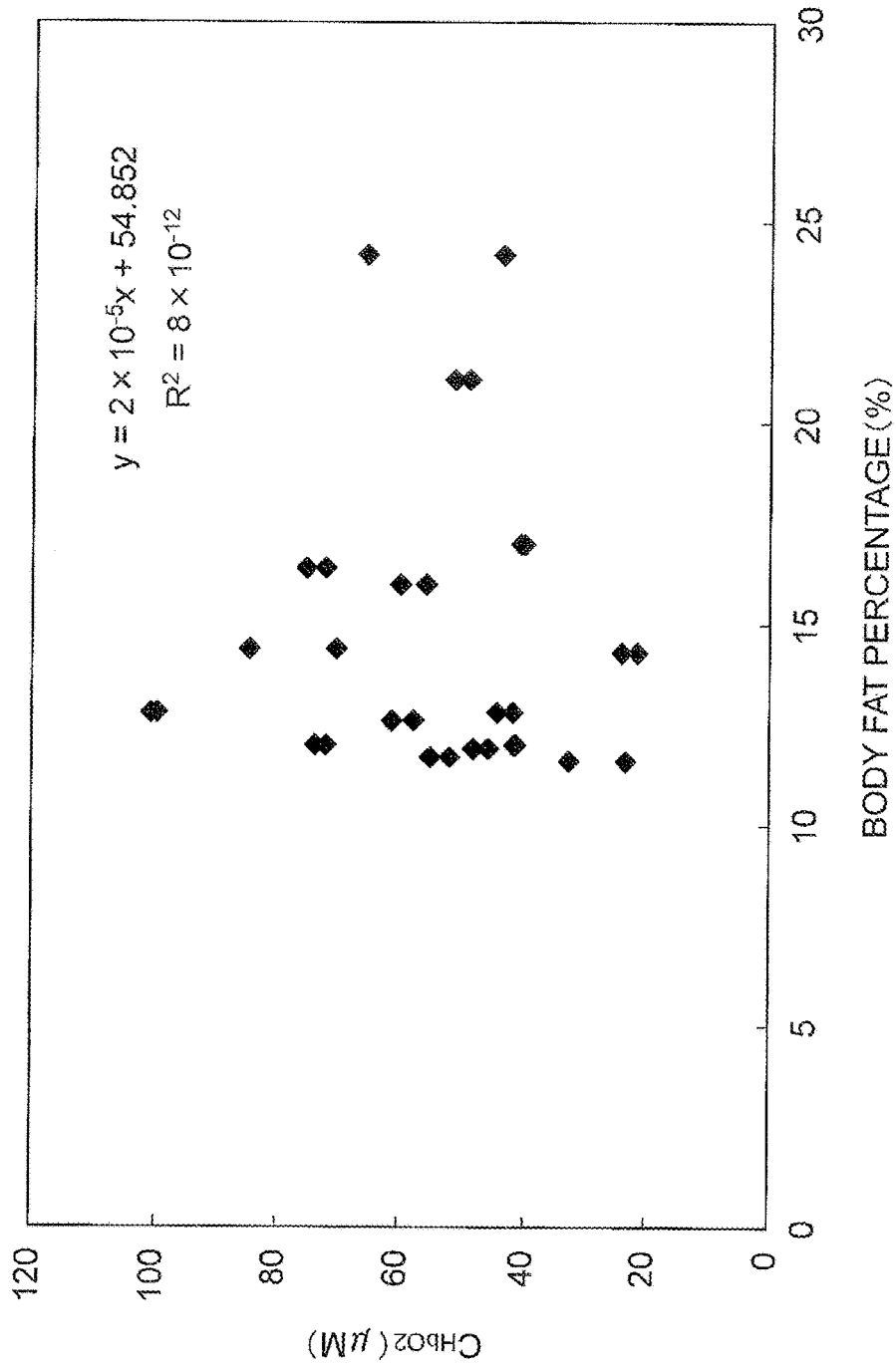
FIG. 13 is a graph showing a relation between corrected oxygenated hemoglobin concentration and body fat percentage in the supraclavicular fossae.
Figure 14:
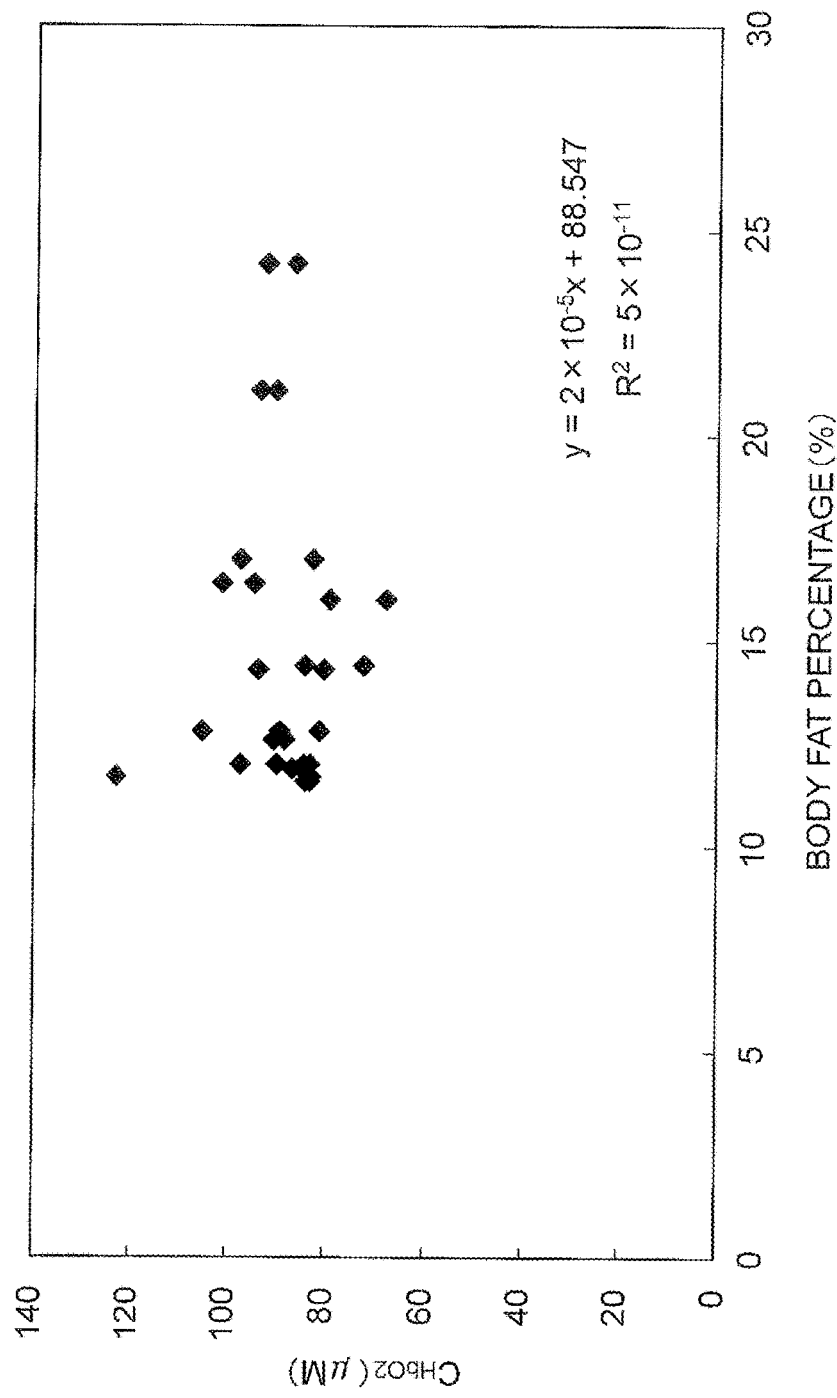
FIG. 14 is a graph showing a relation between corrected oxygenated hemoglobin concentration and body fat percentage in the infraclavicular areas.
Figure 15:
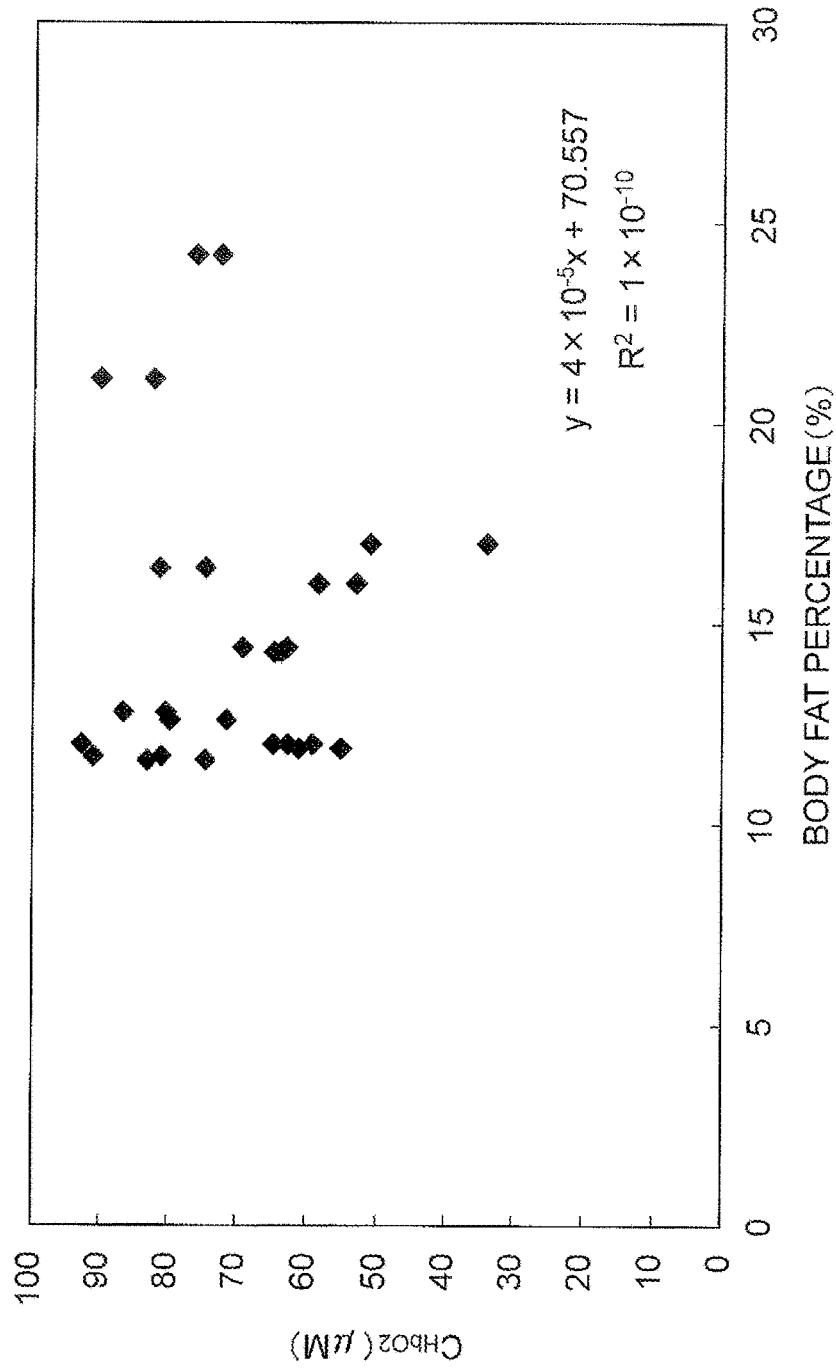
FIG. 15 is a graph showing a relation between corrected oxygenated hemoglobin concentration and body fat percentage in the deltoid muscles.

FIG. 13 to FIG. 15 are graphs showing relations between corrected oxygenated hemoglobin concentration $C_{HbO2}$ and body fat percentage. FIG. 13 shows the relation in the supraclavicular fossae, FIG. 14 the relation in the infraclavicular areas, and FIG. 15 the relation in the deltoid muscles. The vertical axis represents the corrected oxygenated hemoglobin concentration $C_{HbO2}$ (unit: µM) and the horizontal axis the body fat percentage (unit: %). Referring to FIG. 13 to FIG. 15, the slopes of the approximate straight lines and correlation coefficients R are extremely small, whereby it is understood that the oxygenated hemoglobin concentration $C_{HbO2}$ is rarely affected by the body fat percentage.

Figure 16:
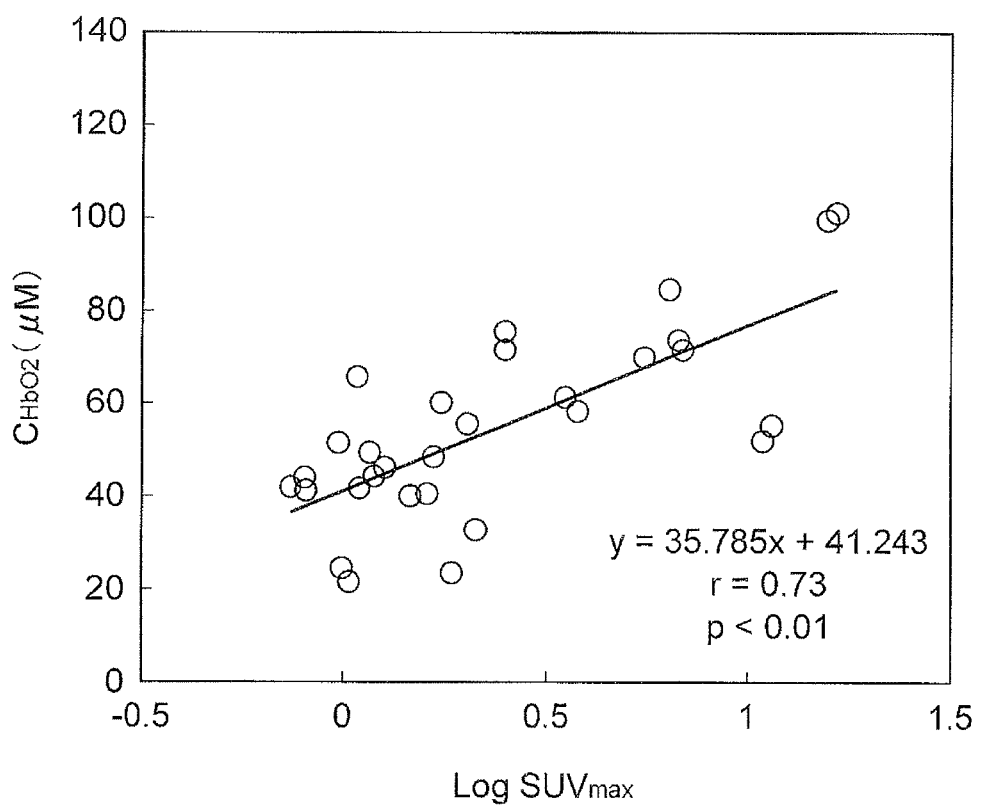
FIG. 16 is a graph showing a relation between corrected oxygenated hemoglobin concentration and activity of BAT in the supraclavicular fossae.
Figure 17:
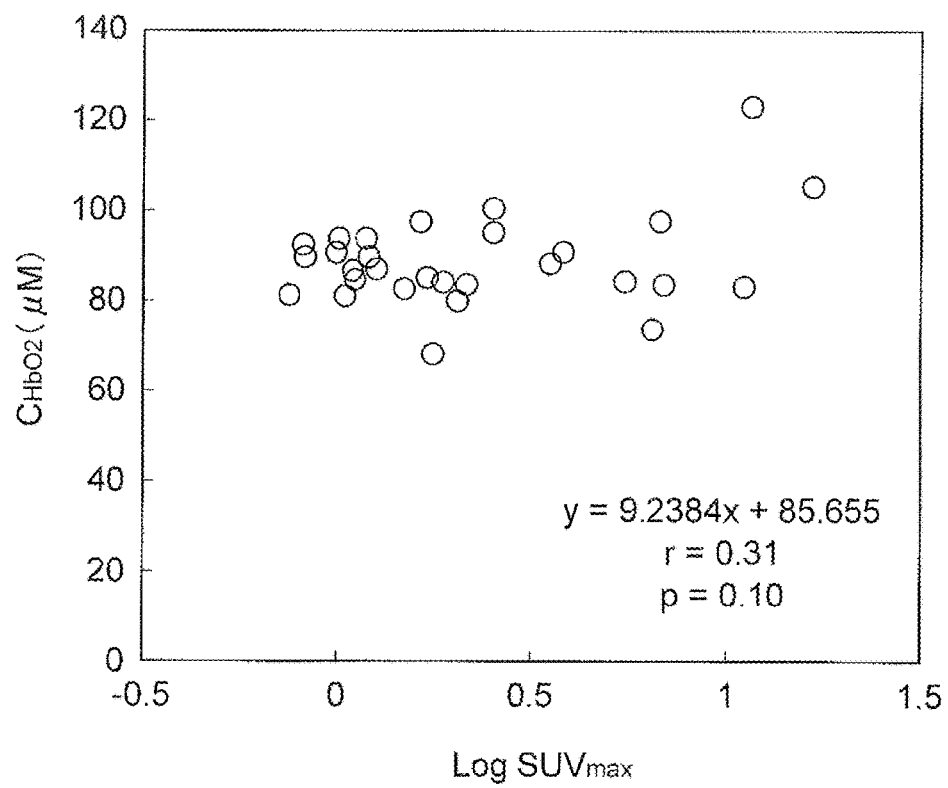
FIG. 17 is a graph showing a relation between corrected oxygenated hemoglobin concentration and activity of BAT in the infraclavicular areas.
Figure 18:
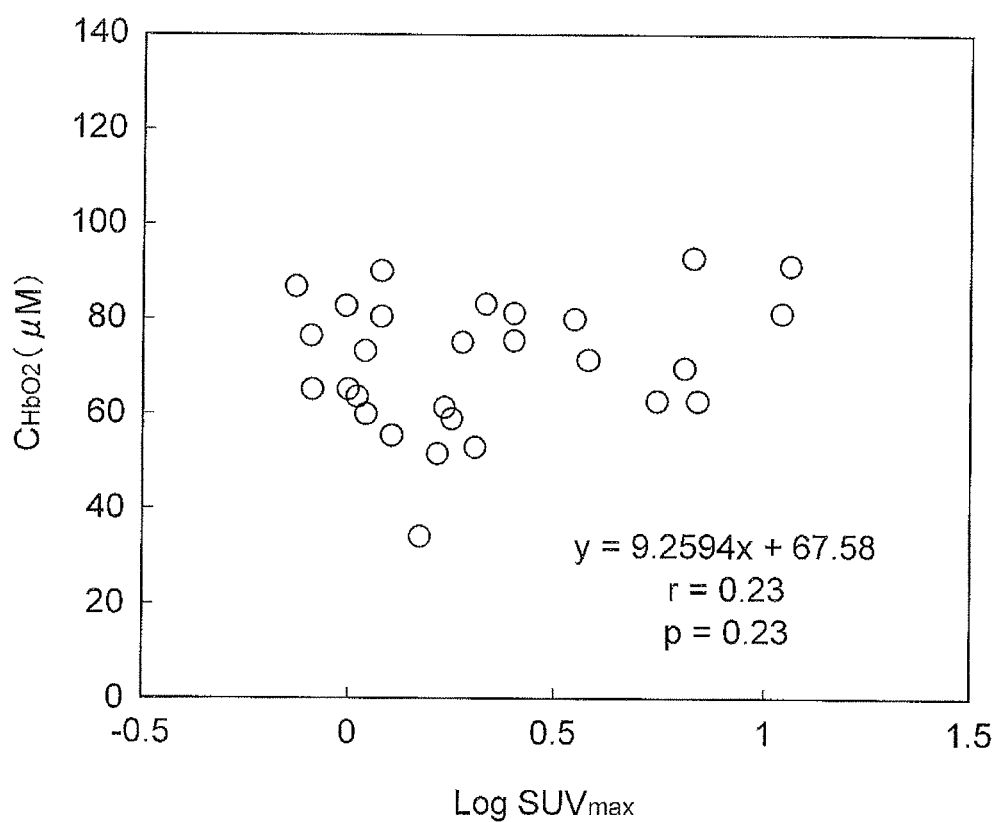
FIG. 18 is a graph showing a relation between corrected oxygenated hemoglobin concentration and activity of BAT in the deltoid muscles.

FIG. 16 to FIG. 18 are graphs showing relations between corrected oxygenated hemoglobin concentration $C_{HbO2}$ and activity $SUV_{max}$ of BAT. FIG. 16 shows the relation in the supraclavicular fossae, FIG. 17 the relation in the infraclavicular areas, and FIG. 18 the relation in the deltoid muscles. The vertical axis represents the oxygenated hemoglobin concentration $C_{HbO2}$ (unit: µM) and the horizontal axis the common logarithm of activity $SUV_{max}$. Referring to FIG. 16 to FIG. 18, a strong correlation was found between oxygenated hemoglobin concentration and activity $SUV_{max}$ of BAT, only in the supraclavicular fossae where BAT exists. Therefore, the activity $SUV_{max}$ of BAT can be accurately evaluated based on the corrected oxygenated hemoglobin concentration $C_{HbO2}$.

When the corrected oxygenated hemoglobin concentrations $C_{HbO2}$ were compared between the six BAT detected subjects and the nine BAT undetected subjects shown in the foregoing Table 1, the values of the BAT detected subjects were significantly high, only in the supraclavicular fossae where BAT exists. FIG. 19 includes graphs showing the comparison, wherein (a) shows average values of corrected oxygenated hemoglobin concentrations $C_{HbO2}$ (unit: µM) in the supraclavicular fossae, (b) those in the infraclavicular areas, and (c) those in the deltoid muscles.

Referring to FIG. 19, it is seen that the corrected oxygenated hemoglobin concentrations $C_{HbO2}$ of the BAT detected subjects are significantly higher than those of the BAT undetected subjects, only in the supraclavicular fossae where BAT exists. Furthermore, only in the supraclavicular fossae, a strong correlation was confirmed between corrected oxygenated hemoglobin concentration $C_{HbO2}$ and activity $SUV_{max}$ of BAT. No such tendency was confirmed in the portions where BAT rarely exists (in the infraclavicular areas and the deltoid muscles).

The present example provided the correlation between activity value $SUV_{max}$ of BAT measured by PET with application of cold stimulation to the subjects and oxygenated hemoglobin concentration $C_{HbO2}$, and the activity value $SUV_{max}$ obtained under the certain load of cold stimulation can be regarded as a BAT amount quantified by PET.

Namely, the result of the present example indicates that in the supraclavicular fossae where BAT exists, the oxygenated hemoglobin concentration $C_{HbO2}$ by the time-resolved spectroscopy reflects a large number of blood capillaries existing in BAT. In other words, the result of the present example indicates that the oxygenated hemoglobin concentration $C_{HbO2}$ can be used for quantitatively evaluating BAT. Therefore, the oxygenated hemoglobin concentration $C_{HbO2}$ by the time-resolved spectroscopy can be defined as an index value for the BAT amount. Furthermore, for example, the oxygenated hemoglobin concentration $C_{HbO2}$ corrected using the parameter for the body fat amount such as the body fat percentage can be used as an index value with higher accuracy.

Figure 20:
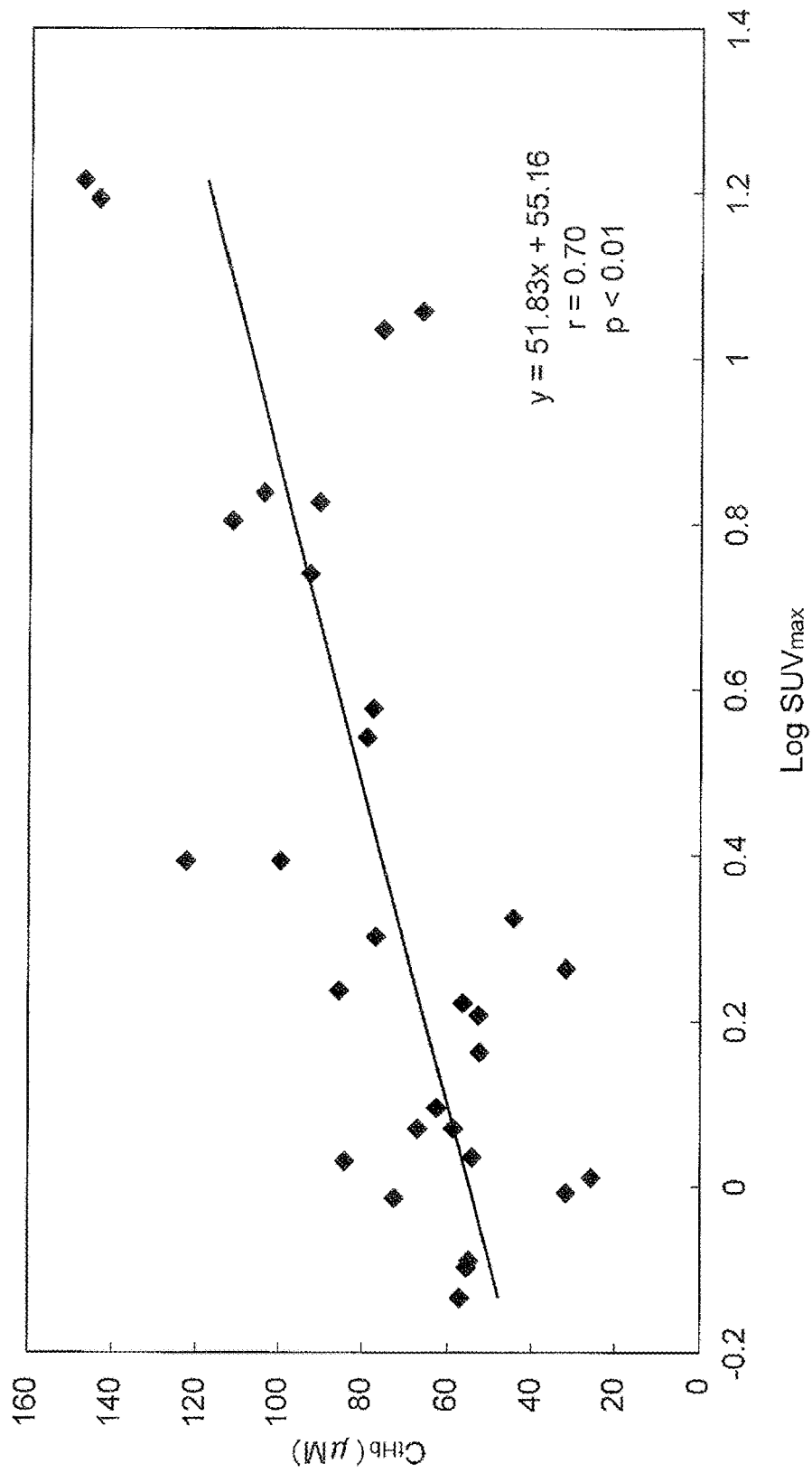
FIG. 20 is a graph showing a relation between total hemoglobin concentration corrected by body fat percentage and activity of BAT in the supraclavicular fossae.
Figure 21:
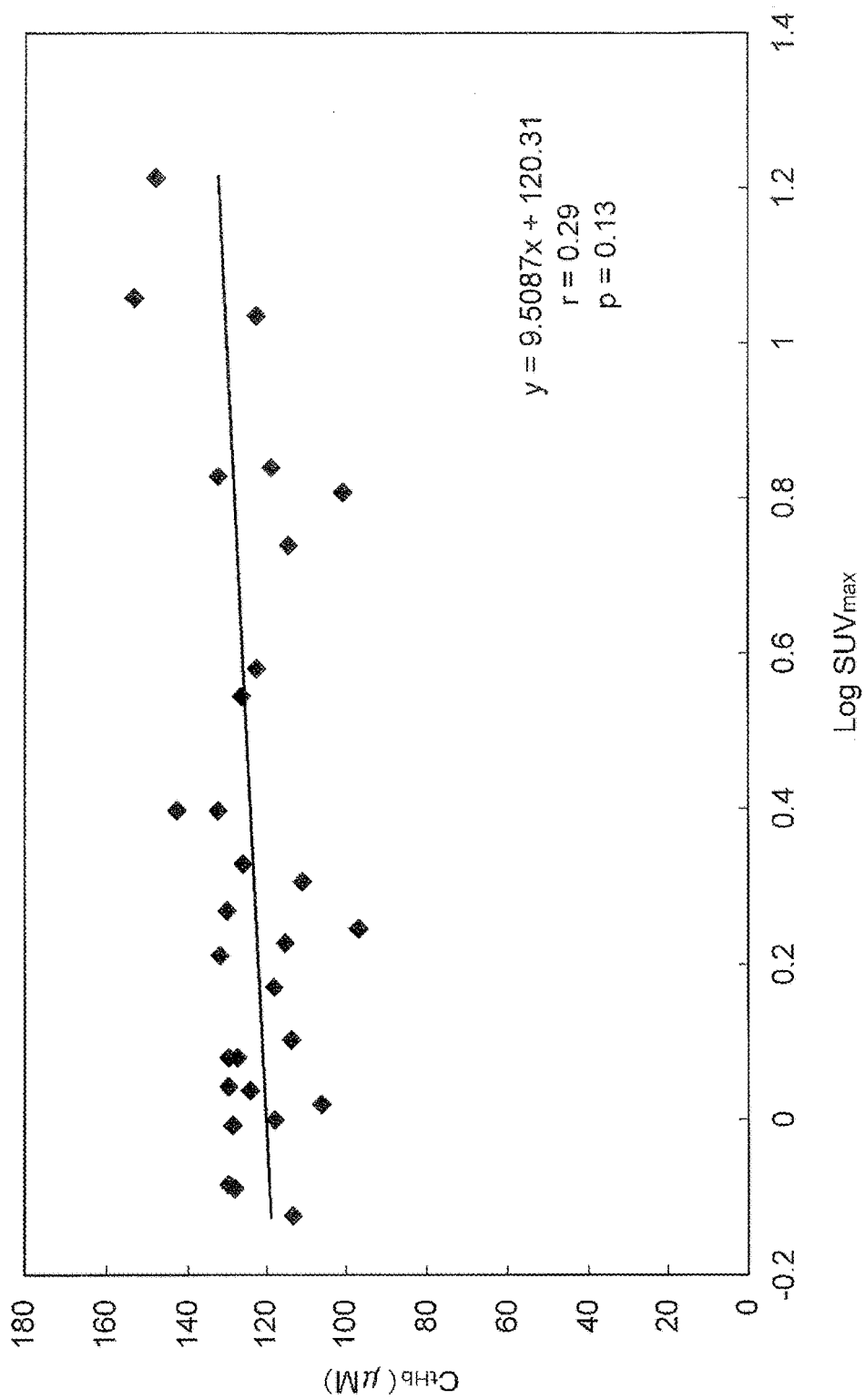
FIG. 21 is a graph showing a relation between total hemoglobin concentration corrected by body fat percentage and activity of BAT in the infraclavicular areas.
Figure 22:
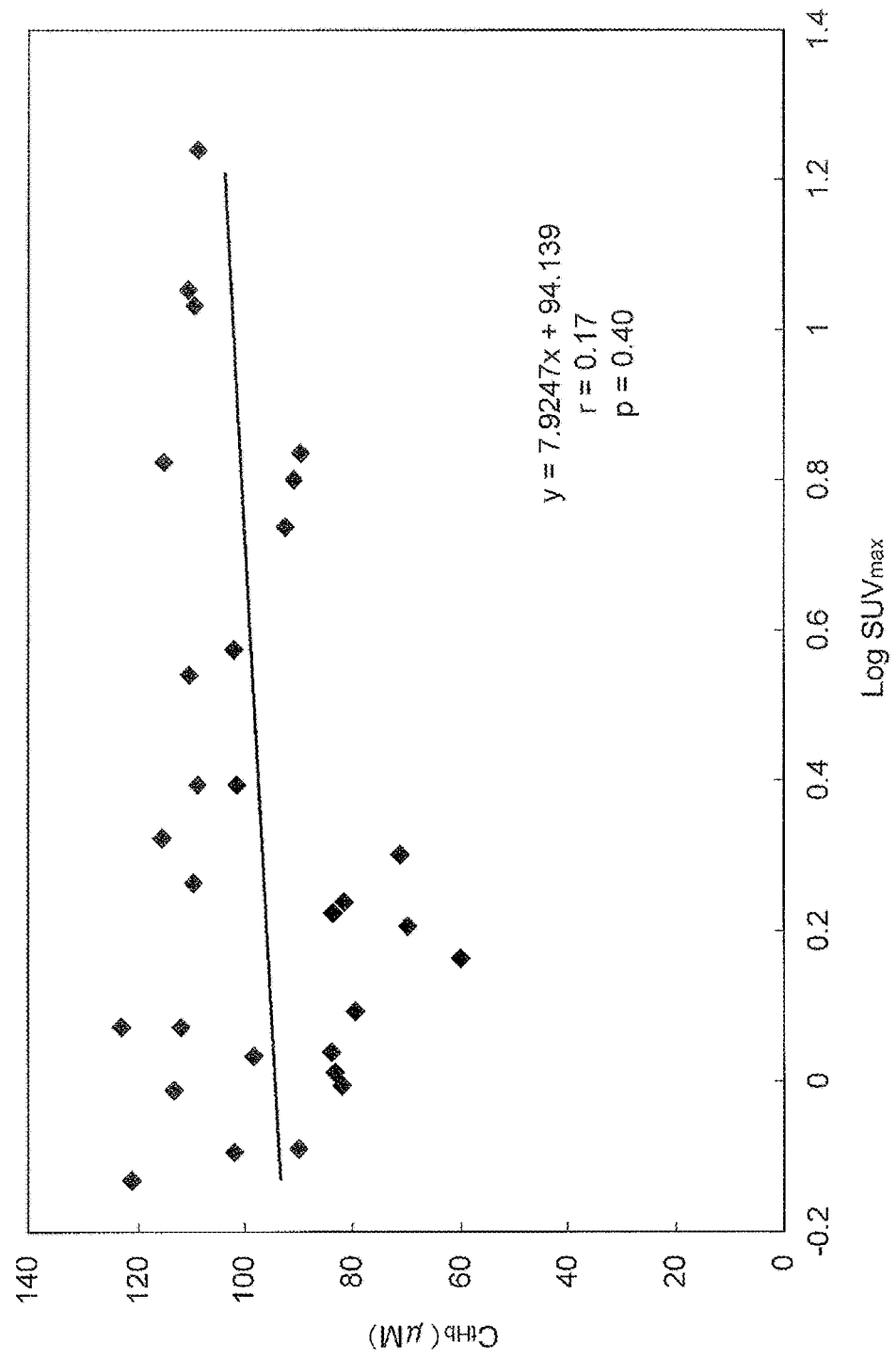
FIG. 22 is a graph showing a relation between total hemoglobin concentration corrected by body fat percentage and activity of BAT in the deltoid muscles.

FIG. 20 to FIG. 22 are graphs showing relations between total hemoglobin concentration $C_{tHb}$ corrected by the body fat percentage and activity $SUV_{max}$ of BAT. FIG. 20 shows the relation in the supraclavicular fossae, FIG. 21 the relation in the infraclavicular areas, and FIG. 22 the relation in the deltoid muscles. The vertical axis represents the total hemoglobin concentration $C_{tHb}$ (unit: µM) and the horizontal axis the common logarithm of activity $SUV_{max}$. Referring to FIG. 20 to FIG. 22, just as in the case of the oxygenated hemoglobin concentration $C_{HbO2}$, a strong correlation was found between total hemoglobin concentration $C_{tHb}$ and activity $SUV_{max}$ of BAT, only in the supraclavicular fossae where BAT exists. Therefore, the total hemoglobin concentration $C_{tHb}$ can also be used as an index value for the BAT amount.

Since the parameter used in calculating the oxygenated hemoglobin concentration $C_{HbO2}$ or the total hemoglobin concentration $C_{tHb}$, e.g., the absorption coefficient $\mu_a$, also increases or decreases depending upon increase or decrease of the oxygenated hemoglobin concentration $C_{HbO2}$ or the total hemoglobin concentration $C_{tHb}$, it is apparent that it has a strong correlation with the activity $SUV_{max}$ of BAT. Therefore, such a parameter can also be used as an index value for the BAT amount.

Figure 23:
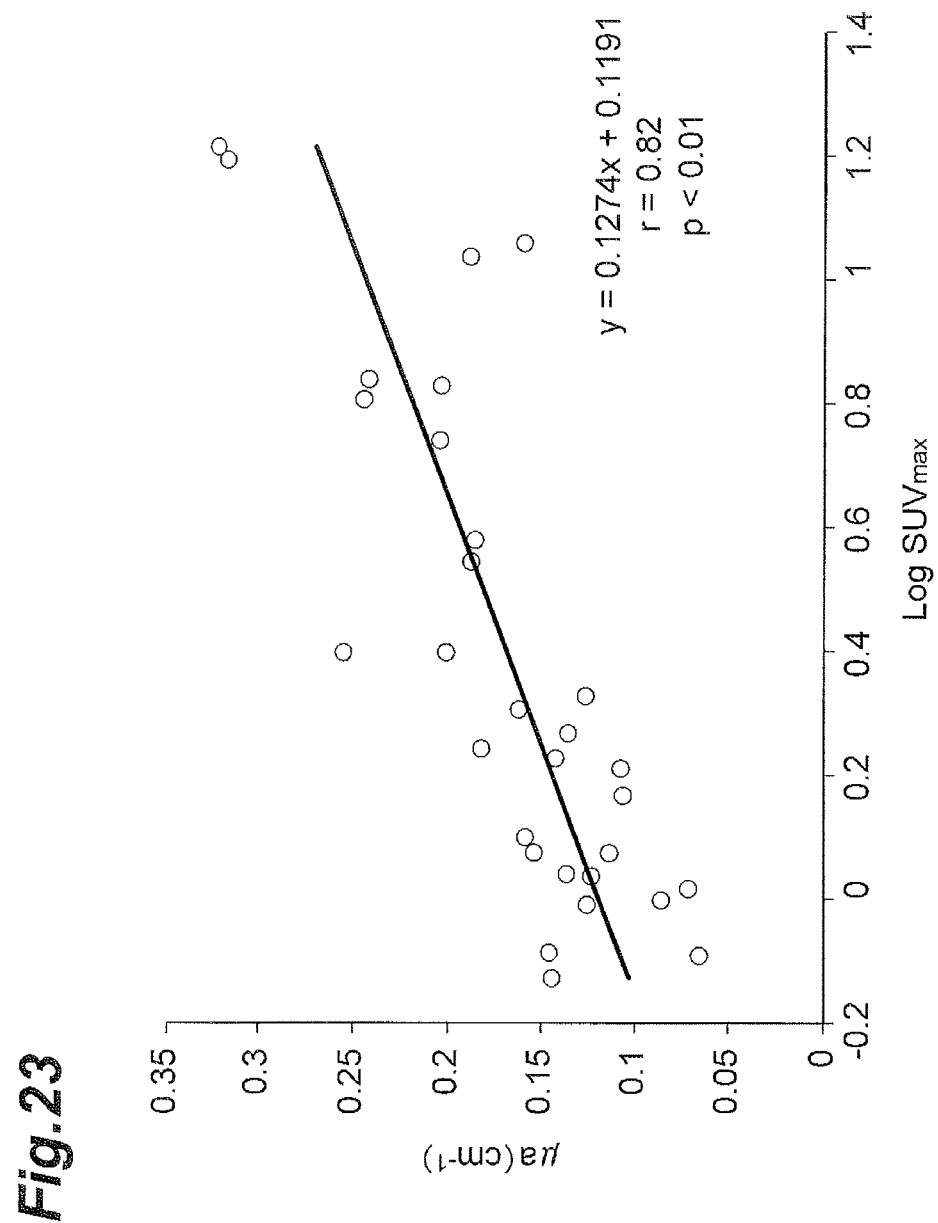
FIG. 23 is a graph showing a relation between absorption coefficient and activity of BAT in the supraclavicular fossae.
Figure 24:
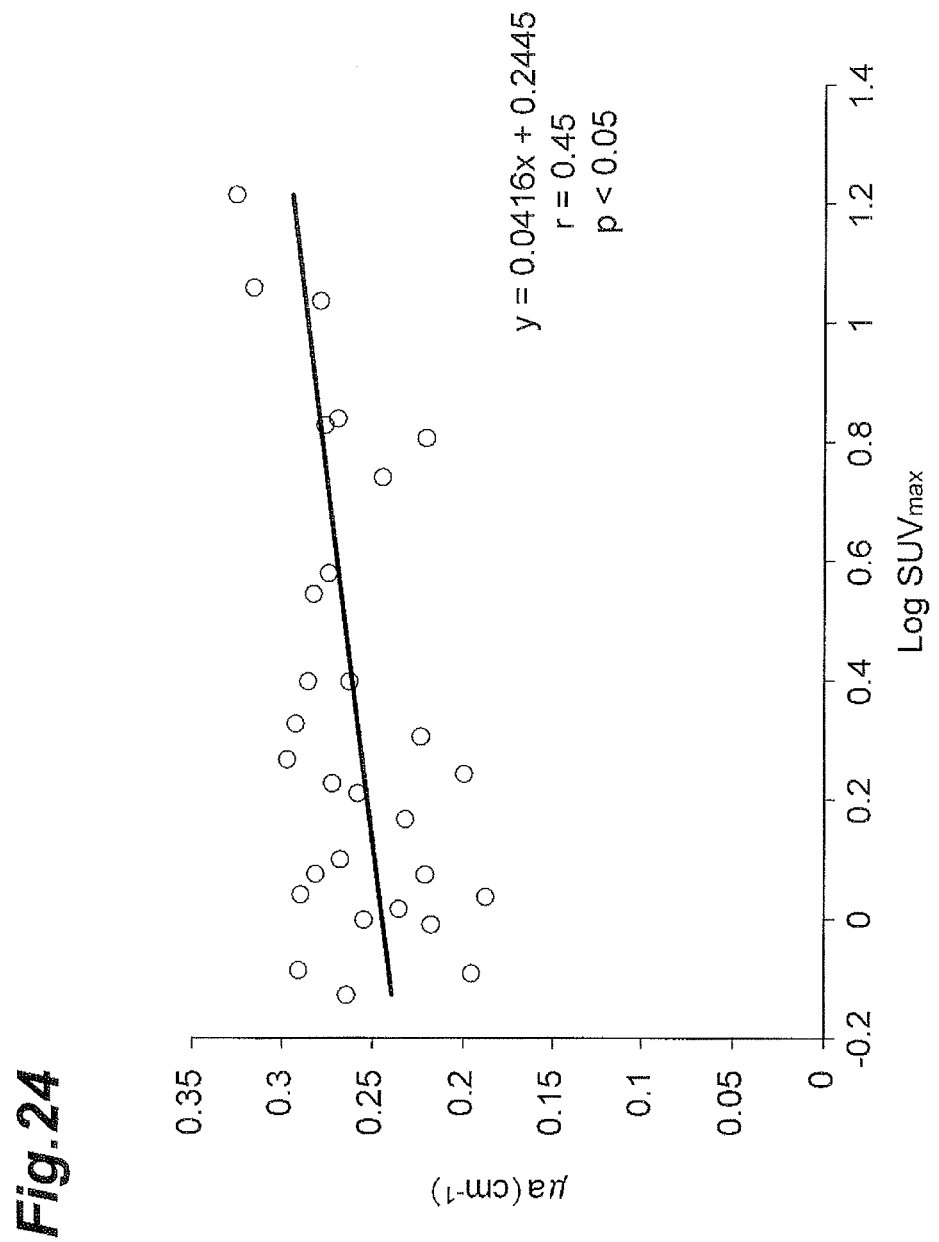
FIG. 24 is a graph showing a relation between absorption coefficient and activity of BAT in the infraclavicular areas.
Figure 25:
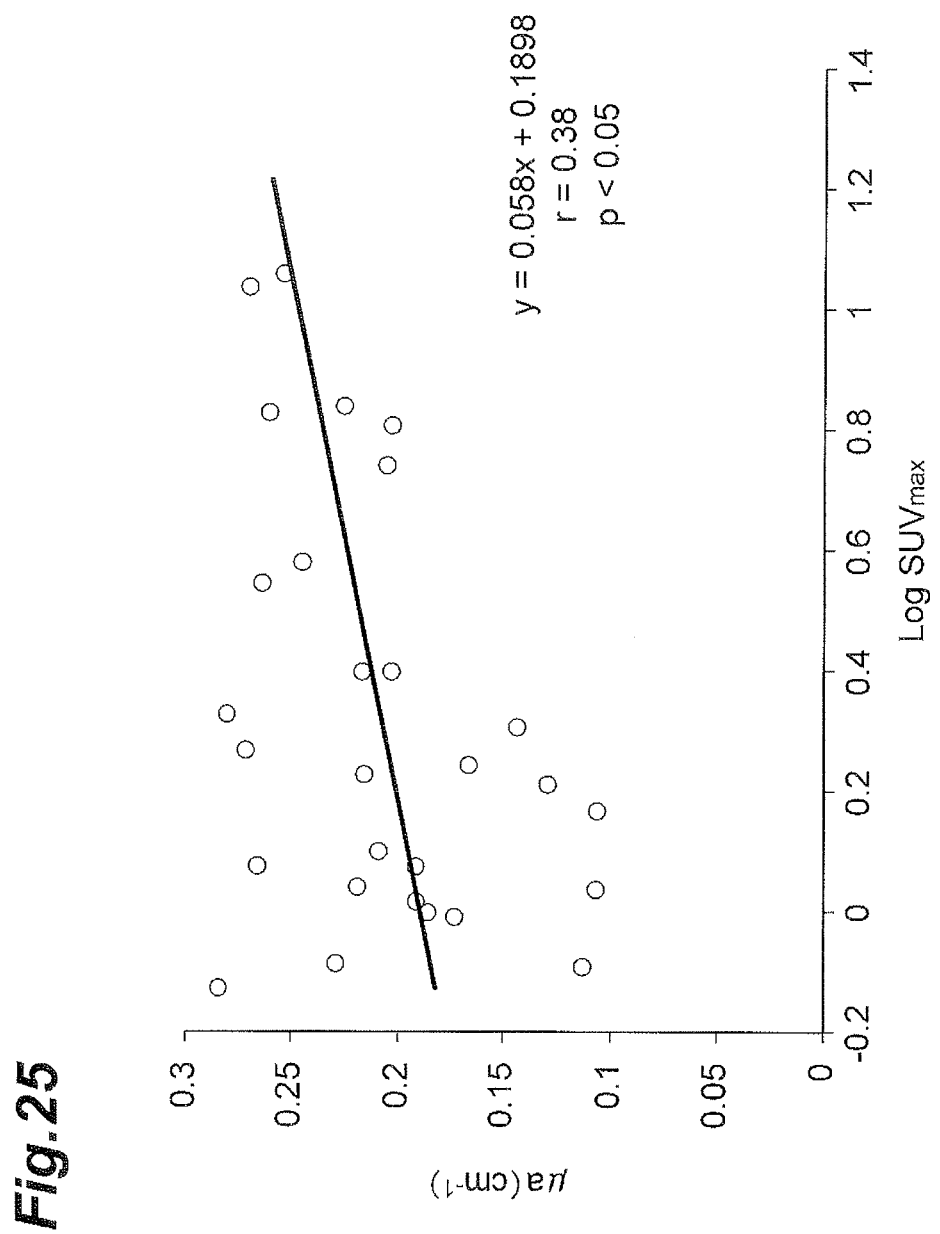
FIG. 25 is a graph showing a relation between absorption coefficient and activity of BAT in the deltoid muscles.

FIG. 23 to FIG. 25 are graphs showing relations between absorption coefficient $\mu_a$ and activity $SUV_{max}$ of BAT. FIG. 23 shows the relation in the supraclavicular fossae, FIG. 24 the relation in the infraclavicular areas, and FIG. 25 the relation in the deltoid muscles. The vertical axis represents the absorption coefficient $\mu_a$ (unit: $cm^{-1}$) and the horizontal axis the common logarithm of activity $SUV_{max}$. It is noted that the absorption coefficients $\mu_a$ are values at the wavelength of 800 nm.

As shown in FIG. 23 to FIG. 25, a certain level of correlation was found between absorption coefficient $\mu_a$ and activity $SUV_{max}$ of BAT, in every measurement target portion. Namely, as the absorption coefficient $\mu_a$ increases, the activity $SUV_{max}$ also becomes larger, not only in the supraclavicular fossae where BAT exists, but also in the infraclavicular areas and deltoid muscles where BAT rarely exists. However, it can be mentioned that there is a significant correlation stronger in the supraclavicular fossae where BAT exists, than in the other measurement target portions.

Figure 26:
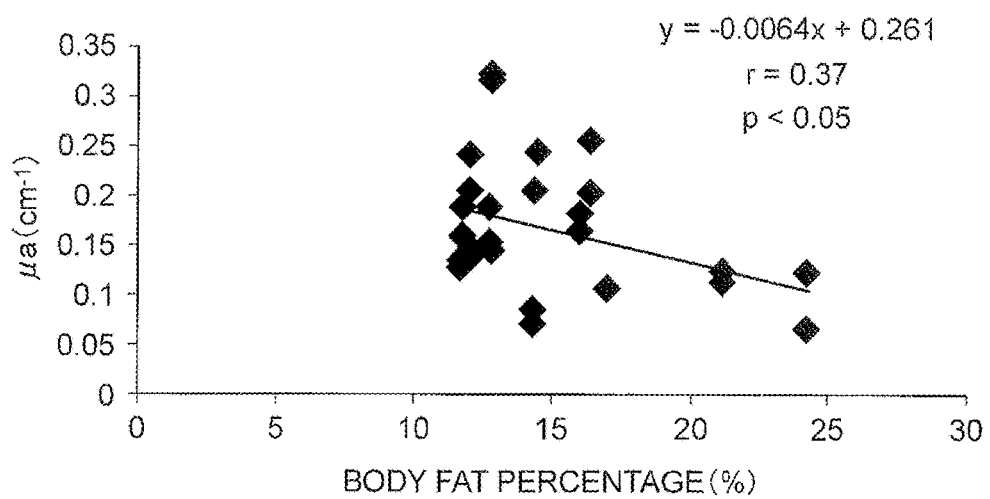
FIG. 26 is a graph showing a correlation between absorption coefficient and body fat percentage in the supraclavicular fossae.
Figure 27:
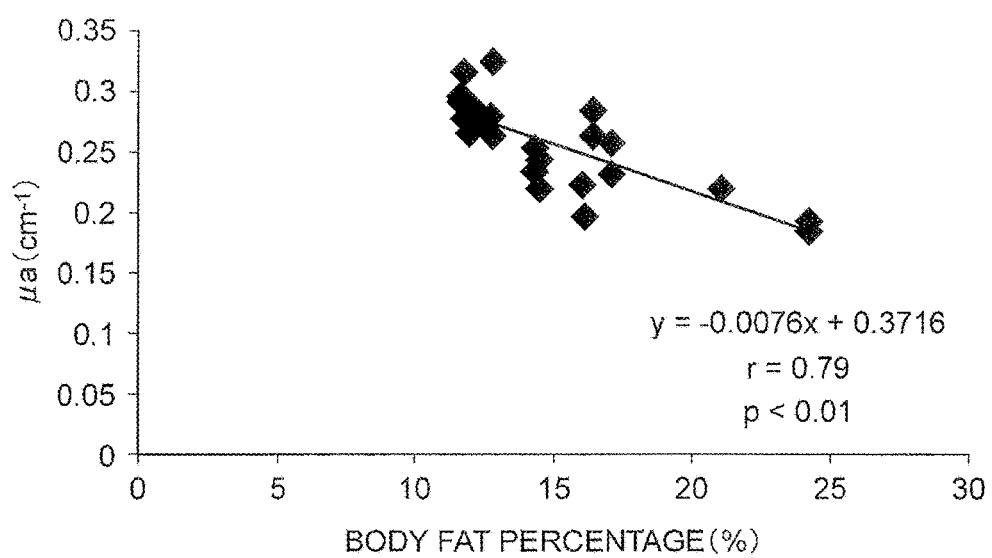
FIG. 27 is a graph showing a correlation between absorption coefficient and body fat percentage in the infraclavicular areas.
Figure 28:
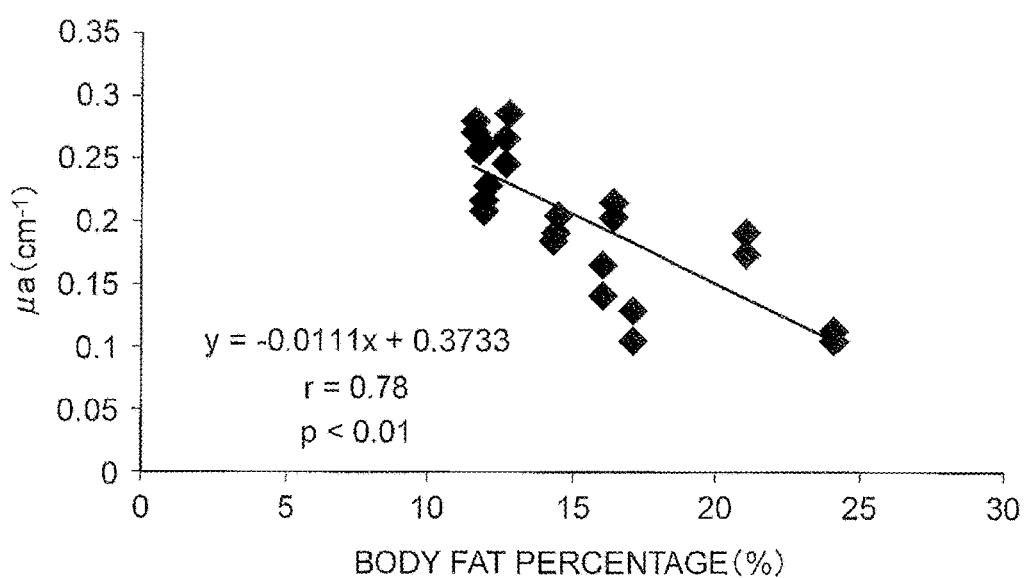
FIG. 28 is a graph showing a correlation between absorption coefficient and body fat percentage in the deltoid muscles.

In order to check the correlation between absorption coefficient $\mu_a$ and body fat percentage, the body fat percentages of the respective subjects were measured. FIG. 26 to FIG. 28 are graphs showing correlations between absorption coefficient $\mu_a$ and body fat percentage. FIG. 26 shows the relation in the supraclavicular fossae, FIG. 27 the relation in the infraclavicular areas, and FIG. 28 the relation in the deltoid muscles. The vertical axis represents the absorption coefficient $\mu_a$ (unit: $cm^{-1}$) and the horizontal axis the body fat percentage (unit: %).

As shown in FIG. 26 to FIG. 28, a certain level of correlation was found between calculated value of absorption coefficient $\mu_a$ and body fat percentage, in every measurement target portion. A conceivable reason for it is that the absorption coefficient measured by the near-infrared spectroscopy is likely to be affected by WAT. Then, correction was made so as to reduce the influence of the body fat percentage on the absorption coefficient $\mu_a$, by use of the aforementioned univariate analysis.

Figure 29:
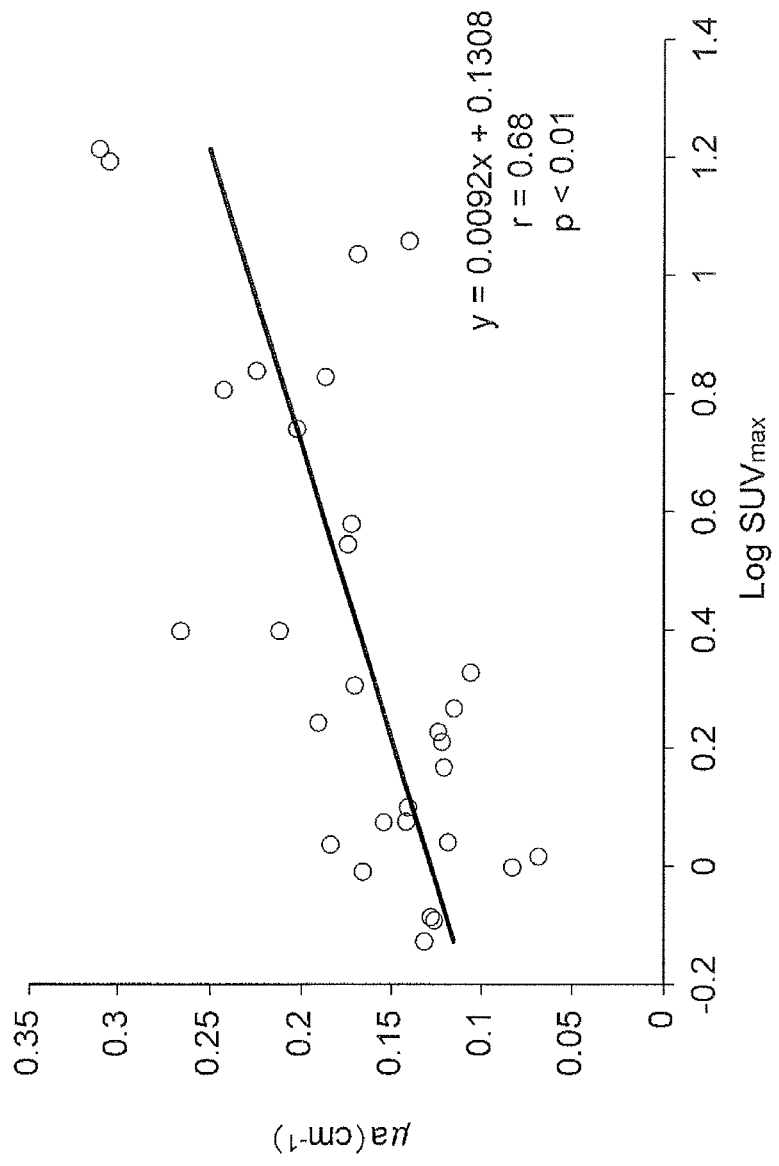
FIG. 29 is a graph showing a relation between corrected absorption coefficient and activity of BAT in the supraclavicular fossae.
Figure 30:
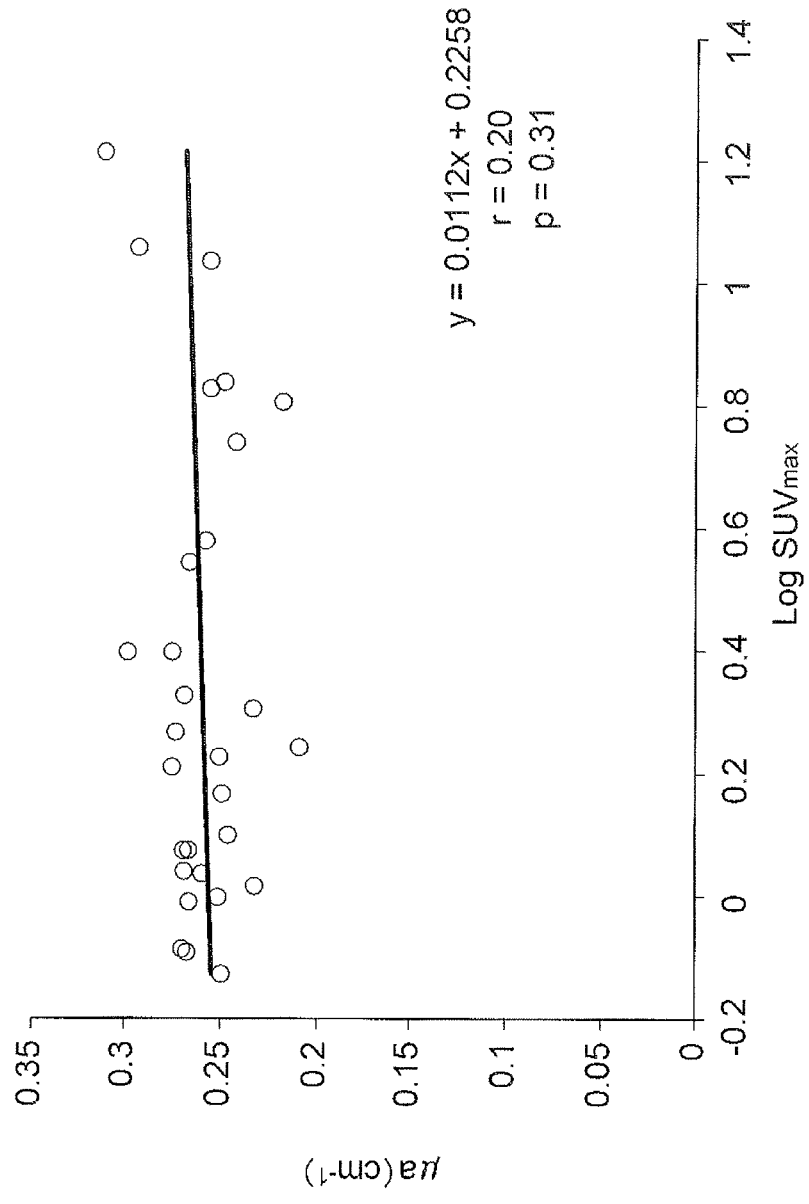
FIG. 30 is a graph showing a relation between corrected absorption coefficient and activity of BAT in the infraclavicular areas.
Figure 31:
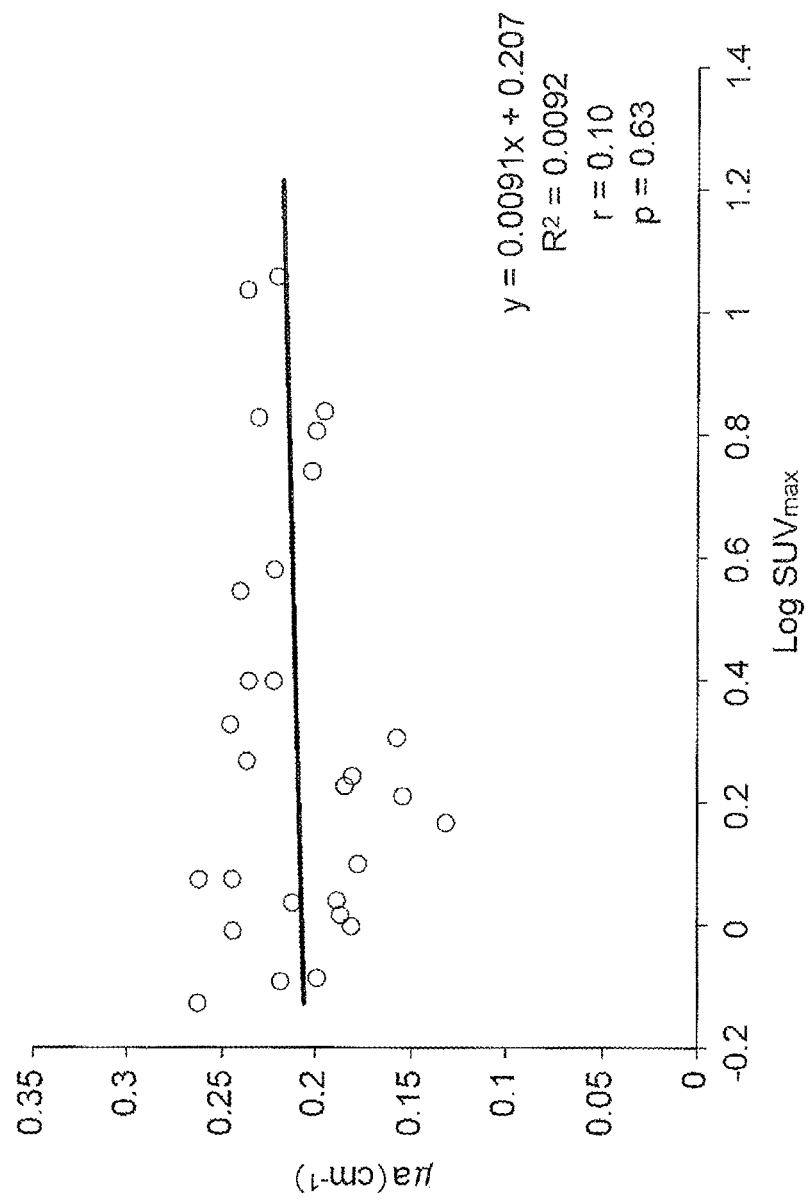
FIG. 31 is a graph showing a relation between corrected absorption coefficient and activity of BAT in the deltoid muscles.

FIG. 29 to FIG. 31 are graphs showing relations between corrected absorption coefficient $\mu_a$ and activity $SUV_{max}$ of BAT. FIG. 29 shows the relation in the supraclavicular fossae, FIG. 30 the relation in the infraclavicular areas, and FIG. 31 the relation in the deltoid muscles. The vertical axis represents the absorption coefficient $\mu_a$ (unit: $cm^{-1}$) and the horizontal axis the common logarithm of activity $SUV_{max}$.

Referring to FIG. 29 to FIG. 31, a strong correlation was found between absorption coefficient $\mu_a$ and activity $SUV_{max}$ of BAT, only in the supraclavicular fossae where BAT exists. Therefore, the activity $SUV_{max}$ of BAT can be accurately evaluated based on the corrected absorption coefficient $\mu_a$. The correction method for the absorption coefficient $\mu_a$ does not have to be limited to the univariate analysis. For example, the correction can be made using another parameter for the body fat amount, instead of the body fat percentage. Examples of other parameters include the thickness of subcutaneous fat, a fat amount estimated from a spectral characteristic, and so on.

Second Embodiment

Figure 32:
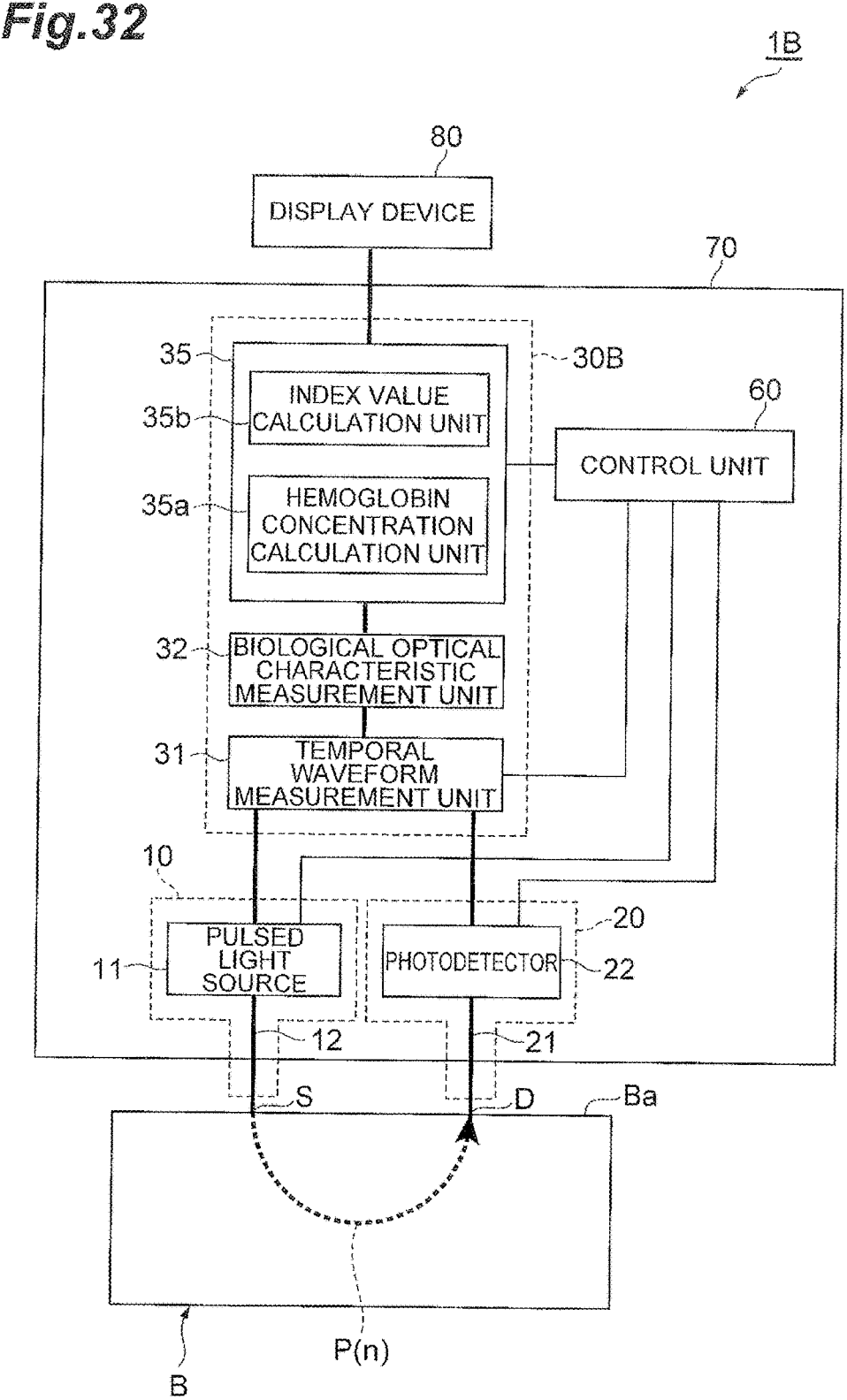
FIG. 32 is a block diagram schematically showing a configuration of the second embodiment of the measurement apparatus.

FIG. 32 is a block diagram schematically showing a configuration of the second embodiment of the measurement apparatus according to the present invention. The measurement apparatus 1B of the present embodiment has a calculation unit 30B, instead of the calculation unit 30 of the measurement apparatus 1A of the first embodiment. This calculation unit 30B includes a calculation processing unit 35, instead of the calculation processing unit 33 of the calculation unit 30 in the first embodiment. The calculation processing unit 35 includes a hemoglobin concentration calculation unit 35a and an index value calculation unit 35b.

The hemoglobin concentration calculation unit 35a acquires the parameter indicating the light absorption characteristic of the measurement target portion B from the biological optical characteristic measurement unit 32 and performs a predetermined calculation operation to calculate a deoxygenated hemoglobin concentration ($C_{Hb}$) in the measurement target portion B. A calculation method for the deoxygenated hemoglobin concentration ($C_{Hb}$) is the same as in the first embodiment. The measurement apparatus 1B, different from the measurement apparatus 1A, is not provided with the storage unit 40 and the parameter input unit 50.

In the present embodiment, the biological optical characteristic measurement unit 32 calculates the scattering coefficient $\mu'_s$ of the measurement target portion B, based on the temporal waveform obtained by the temporal waveform measurement unit 31. It is noted that, in the description below, the scattering coefficient $\mu'_s$ is a concept including the reduced scattering coefficient. The index value calculation unit 35b acquires the scattering coefficient of the measurement target portion B from the biological optical characteristic measurement unit 32 and calculates the index value for the BAT amount from at least one value of the deoxygenated hemoglobin concentration ($C_{Hb}$) calculated by the hemoglobin concentration calculation unit 35a and the scattering coefficient $\mu'_s$ calculated by the biological optical characteristic measurement unit 32.

A flowchart of the operation of the measurement apparatus 1B and the measurement method according to the present embodiment is the same as in FIG. 4. In the present embodiment, however, step S13 is modified to calculate the index value for the BAT amount from at least one value of the scattering coefficient $\mu'_s$ and the deoxygenated hemoglobin concentration ($C_{Hb}$).

As in Example described below, the Inventors found out after research that there was a significant correlation of the BAT amount with the scattering coefficient $\mu'_s$ and the deoxygenated hemoglobin concentration ($C_{Hb}$). Therefore, the measurement apparatus 1B and measurement method of the present embodiment described above can markedly reduce the burden on the subject and can perform the measurement of BAT extremely simply as in the first embodiment.

Second Example

Figure 33:
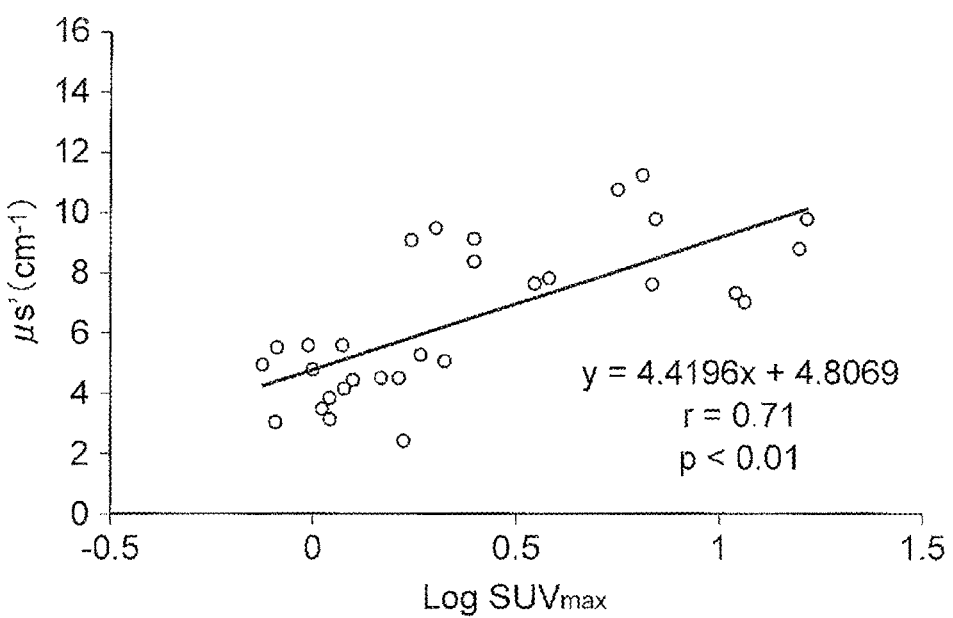
FIG. 33 is a graph showing a relation between scattering coefficient and activity of BAT in the supraclavicular fossae.
Figure 34:
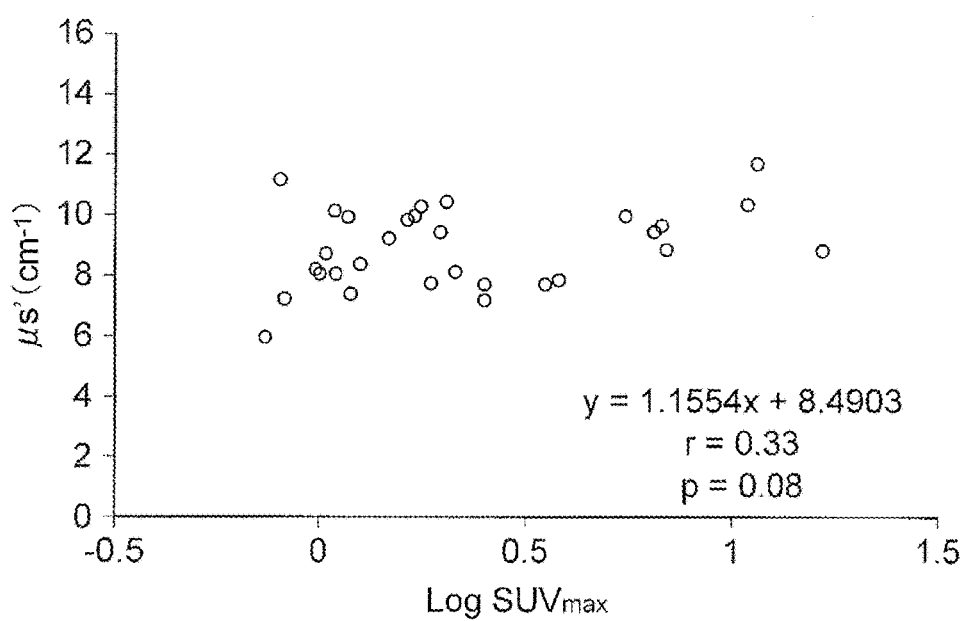
FIG. 34 is a graph showing a relation between scattering coefficient and activity of BAT in the infraclavicular areas.
Figure 35:
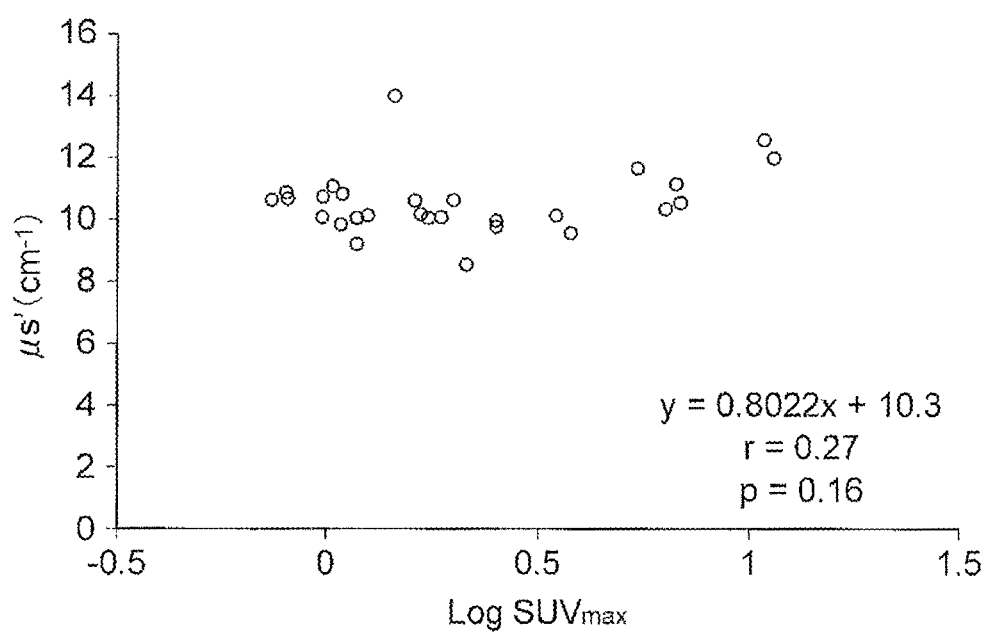
FIG. 35 is a graph showing a relation between scattering coefficient and activity of BAT in the deltoid muscles.

The following will describe the result of an experiment to check the correlation of BAT activity value with the scattering coefficient $\mu'_s$ and the deoxygenated hemoglobin concentration ($C_{Hb}$) for a plurality of subjects, conducted by the Inventors. This experiment was carried out by the same method as in the first example. FIG. 33 to FIG. 35 are graphs showing relations between scattering coefficient $\mu'_s$ and activity $SUV_{max}$ of BAT. FIG. 33 shows the relation in the supraclavicular fossae, FIG. 34 the relation in the infraclavicular areas, and FIG. 35 the relation in the deltoid muscles. The vertical axis represents the scattering coefficient $\mu'_s$ (unit: cm$^{-1}$) and the horizontal axis the common logarithm of activity $SUV_{max}$. It is noted that the scattering coefficients $\mu'_s$ are values at the wavelength of 760 nm.

Referring to FIG. 33 to FIG. 35, a strong correlation was found between scattering coefficient $\mu'_s$ and activity $SUV_{max}$ of BAT, only in the supraclavicular fossae where BAT exists. Therefore, the activity $SUV_{max}$ of BAT can be accurately evaluated based on the scattering coefficient $\mu'_s$.

Figure 36:
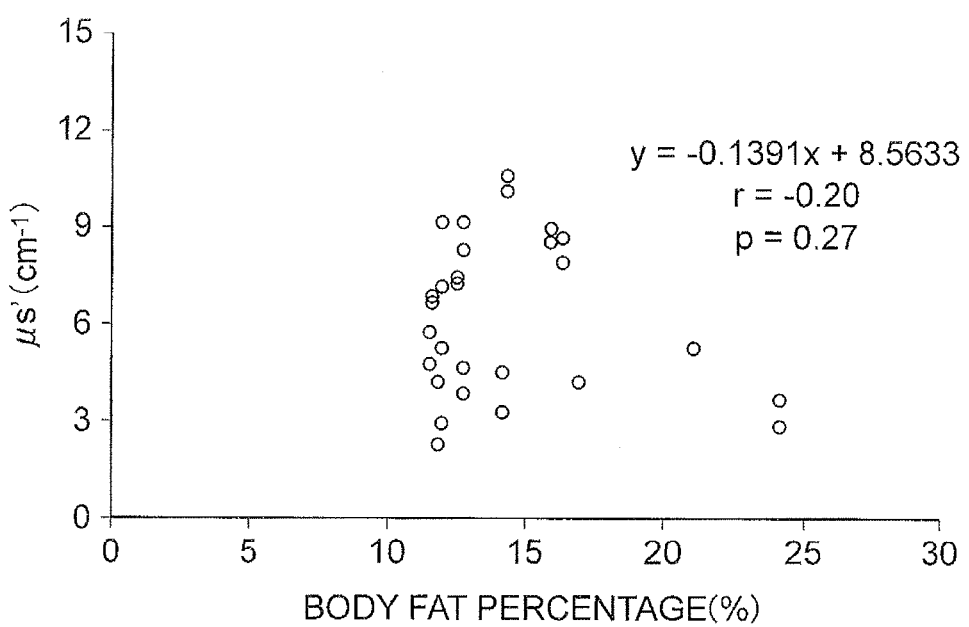
FIG. 36 is a graph showing a correlation between scattering coefficient and body fat percentage in the supraclavicular fossae.
Figure 37:
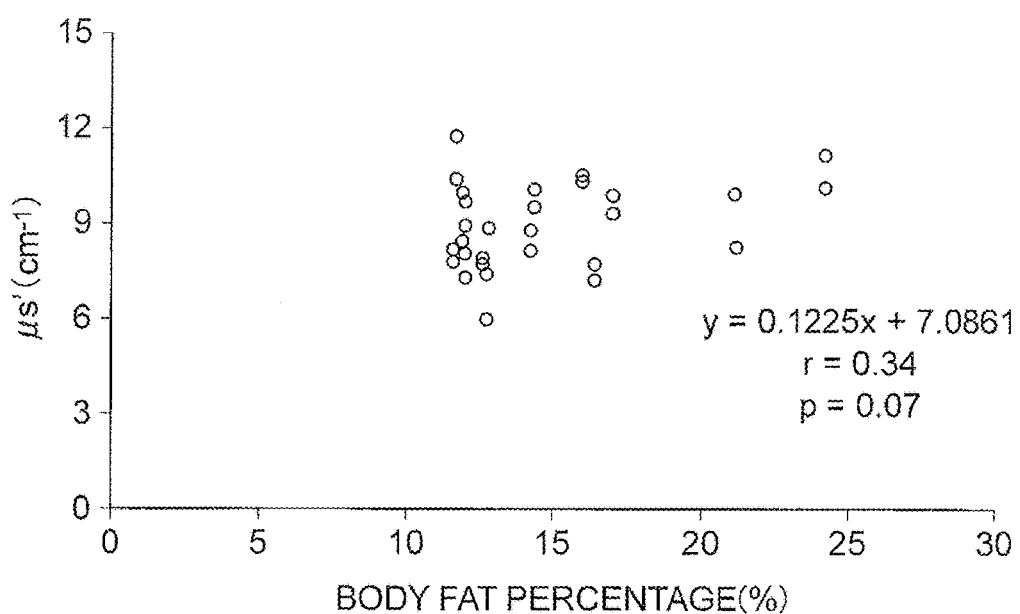
FIG. 37 is a graph showing a correlation between scattering coefficient and body fat percentage in the infraclavicular areas.
Figure 38:
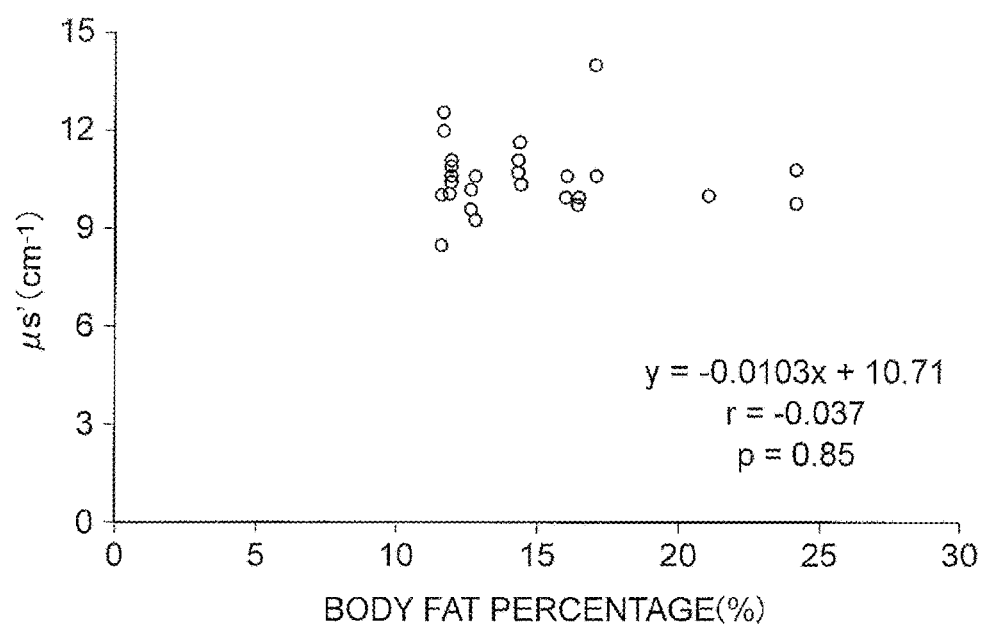
FIG. 38 is a graph showing a correlation between scattering coefficient and body fat percentage in the deltoid muscles.

In order to check the correlation between scattering coefficient $\mu'_s$ and body fat percentage, the body fat percentages of the respective subjects were measured. FIG. 36 to FIG. 38 are graphs showing correlations between scattering coefficient $\mu'_s$ and body fat percentage. FIG. 36 shows the relation in the supraclavicular fossae, FIG. 37 the relation in the infraclavicular areas, and FIG. 38 the relation in the deltoid muscles. The vertical axis represents the scattering coefficient $\mu'_s$ (unit: cm$^{-1}$) and the horizontal axis the body fat percentage (unit: %).

As shown in FIG. 36 to FIG. 38, there is little correlation confirmed between calculated value of scattering coefficient $\mu'_s$ and body fat percentage, in any one of the measurement target portions. A conceivable reason for it is that the correlation between BAT amount and scattering coefficient $\mu'_s$ is attributed to mitochondria in BAT cells and the body fat percentage does not affect the scattering coefficient $\mu'_s$. Therefore, when the index value for the BAT amount is calculated from the scattering coefficient $\mu'_s$, it can be accurately calculated without correction using the body fat percentage.

Figure 39:
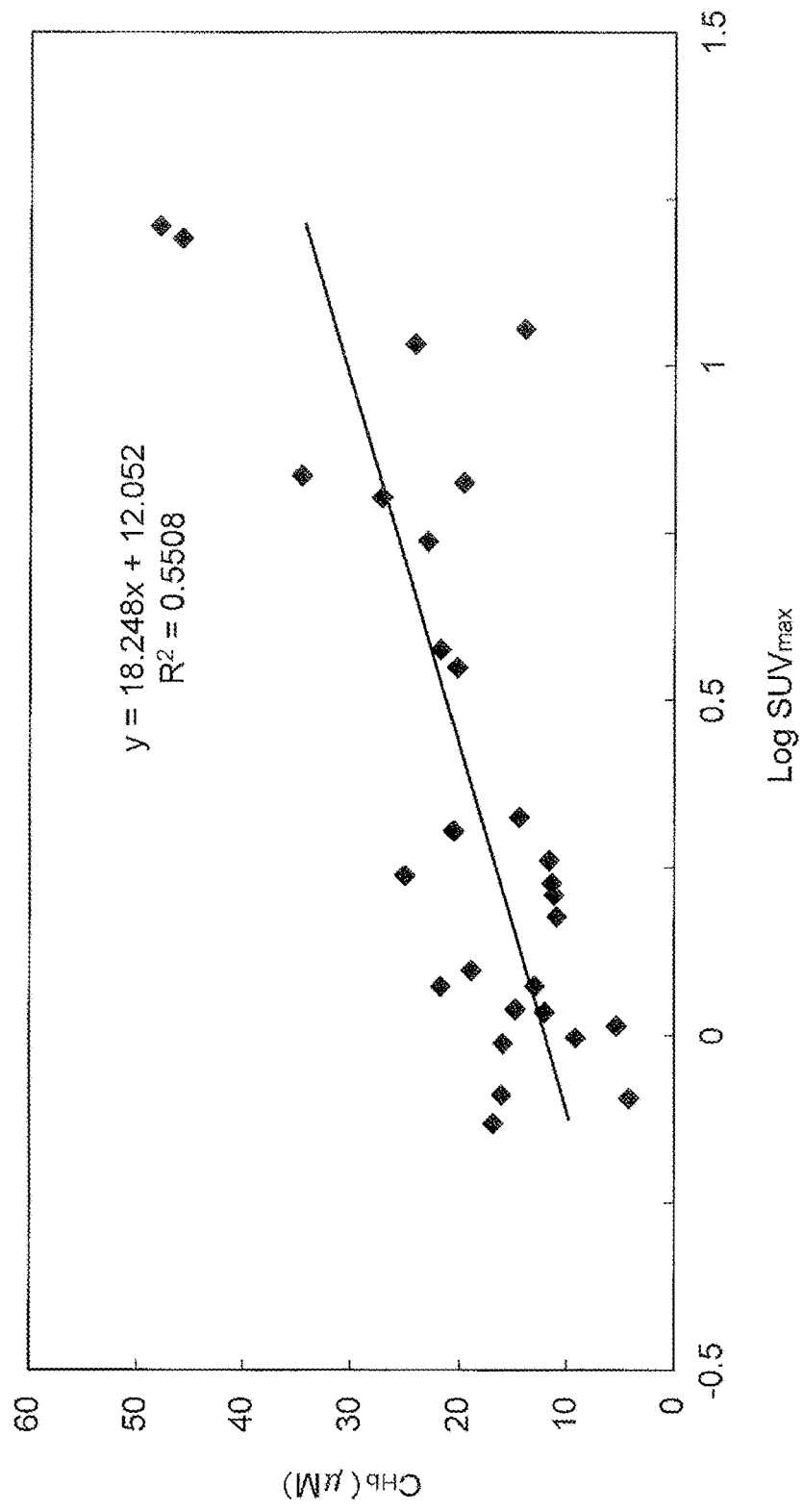
FIG. 39 is a graph showing a relation between deoxygenated hemoglobin concentration and activity of BAT in the supraclavicular fossae.

FIG. 39 is a graph showing a relation between deoxygenated hemoglobin concentration ($C_{Hb}$) and activity $SUV_{max}$ of BAT, and shows the relation in the supraclavicular fossae. The vertical axis represents the deoxygenated hemoglobin concentration ($C_{Hb}$) (unit: μM) and the horizontal axis the common logarithm of activity $SUV_{max}$. Referring to FIG. 39, a strong correlation was found between deoxygenated hemoglobin concentration ($C_{Hb}$) and activity $SUV_{max}$ of BAT, in the supraclavicular fossae where BAT exists. Therefore, the activity $SUV_{max}$ of BAT can be accurately evaluated based on the deoxygenated hemoglobin concentration ($C_{Hb}$).

Figure 40:
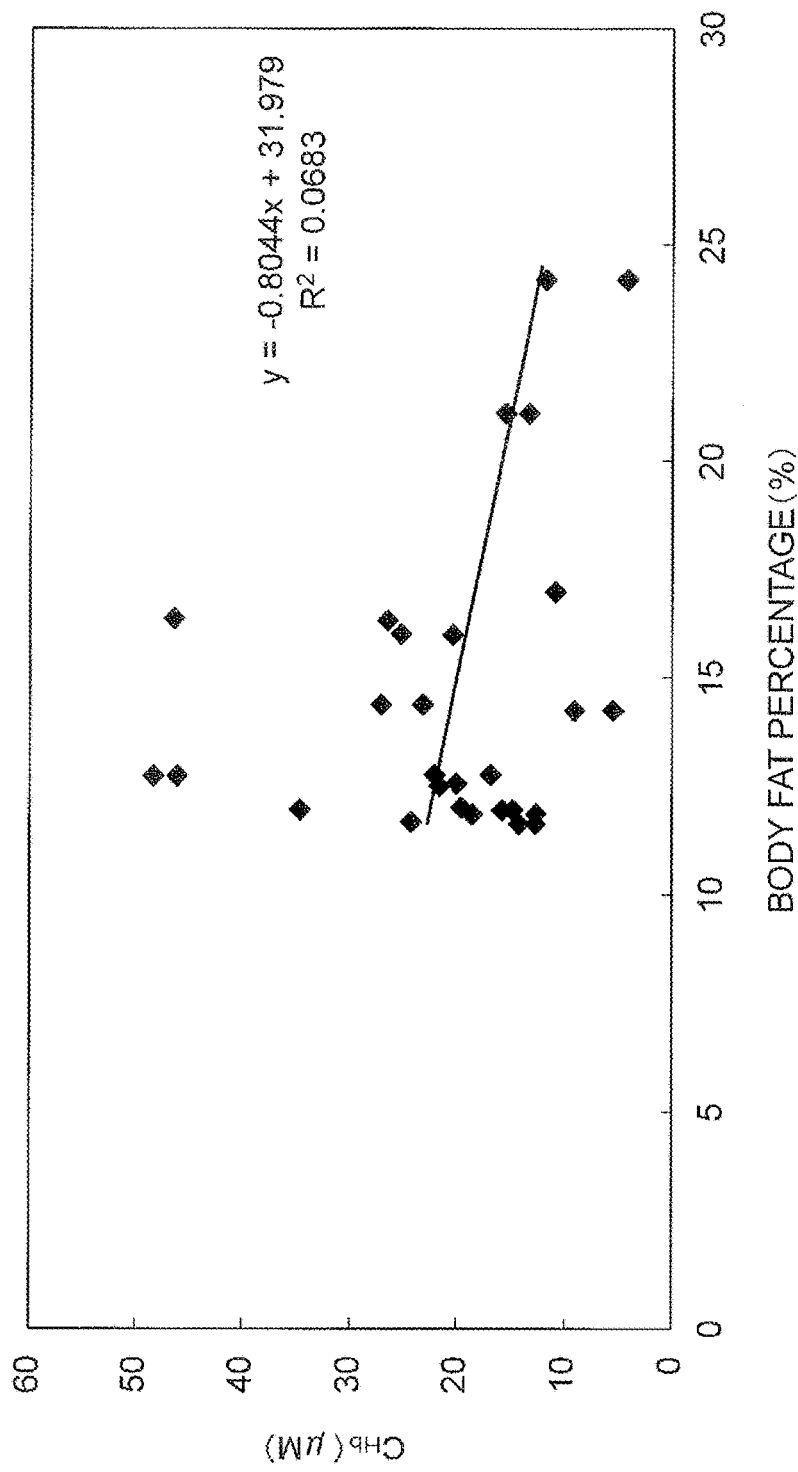
FIG. 40 is a graph showing a correlation between deoxygenated hemoglobin concentration and body fat percentage in the supraclavicular fossae.

In order to check the correlation between deoxygenated hemoglobin concentration ($C_{Hb}$) and body fat percentage, the body fat percentages of the respective subjects were measured. FIG. 40 is a graph showing a correlation between deoxygenated hemoglobin concentration ($C_{Hb}$) and body fat percentage, and shows the relation in the supraclavicular fossae. The vertical axis represents the deoxygenated hemoglobin concentration ($C_{Hb}$) (unit: μM) and the horizontal axis the body fat percentage (unit: %). As shown in FIG. 40, there is little correlation confirmed between calculated value of deoxygenated hemoglobin concentration ($C_{Hb}$) and body fat percentage. Therefore, when the index value for the BAT amount is calculated from the deoxygenated hemoglobin concentration ($C_{Hb}$), it can be accurately calculated without correction using the body fat percentage.

Third Embodiment

Figure 41:
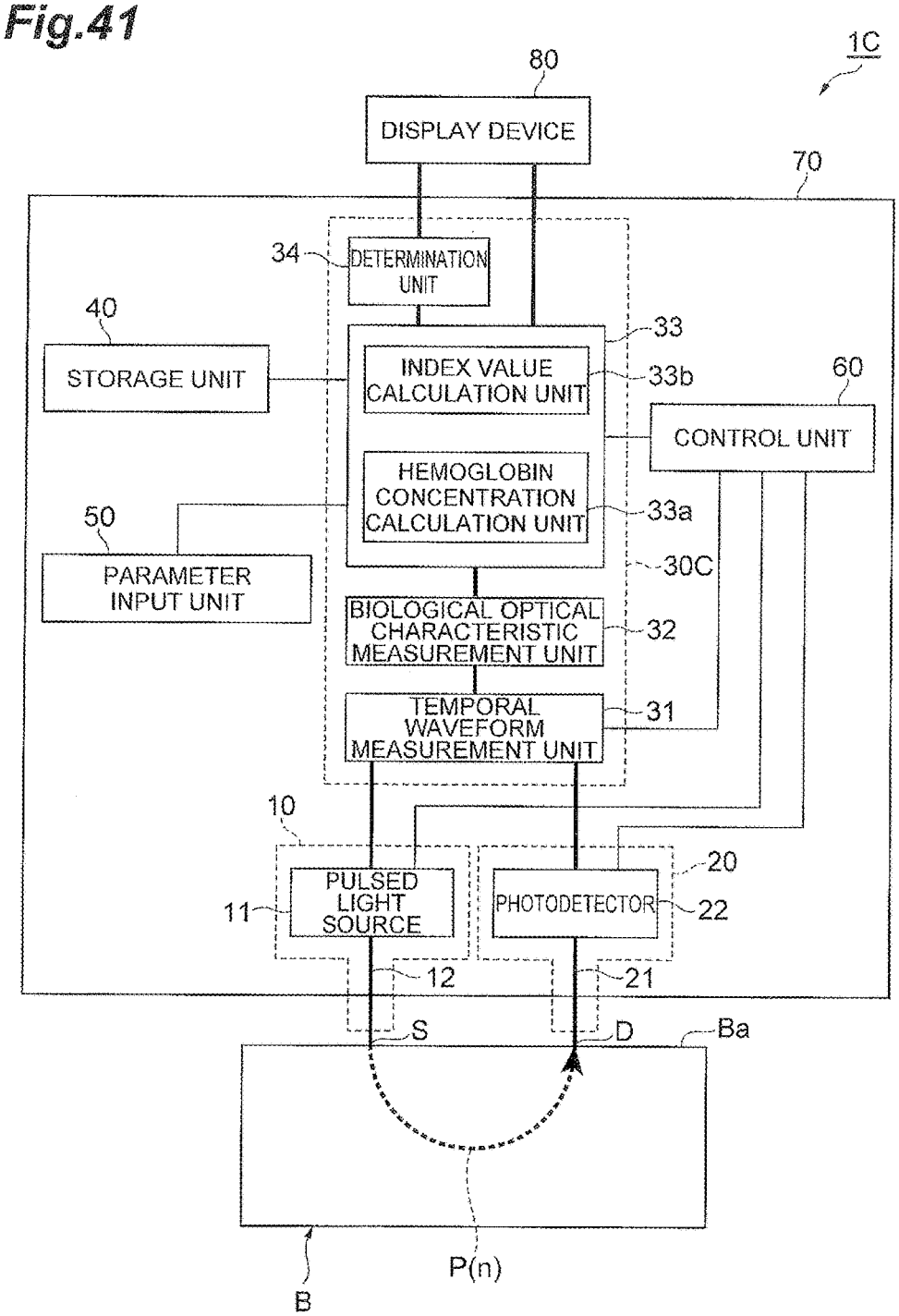
FIG. 41 is a block diagram schematically showing a configuration of the third embodiment of the measurement apparatus.

FIG. 41 is a block diagram schematically showing a configuration of the third embodiment of the measurement apparatus according to the present invention. The measurement apparatus 1C of the present embodiment has a calculation unit 30C, instead of the calculation unit 30 of the measurement apparatus 1A of the first embodiment. This calculation unit 30C further has a determination unit 34, in addition to the configuration of the calculation unit 30 in the first embodiment. Since the configuration of the calculation unit 30C except for the determination unit 34 is the same as that of the calculation unit 30, the detailed description thereof is omitted herein.

The determination unit 34 is provided with the index value for the BAT amount from the index value calculation unit 33b of the calculation processing unit 33. The determination unit 34 compares this index value with a predetermined threshold value to determine whether the BAT amount of a subject is negative or positive. Specifically, the determination unit 34 determines that it is positive if the index value exceeds the threshold value and determines that it is negative unless the index value exceeds the threshold value. This determination result is displayed together with the index value for the BAT amount, for example, on the display device 80.

Figure 42:
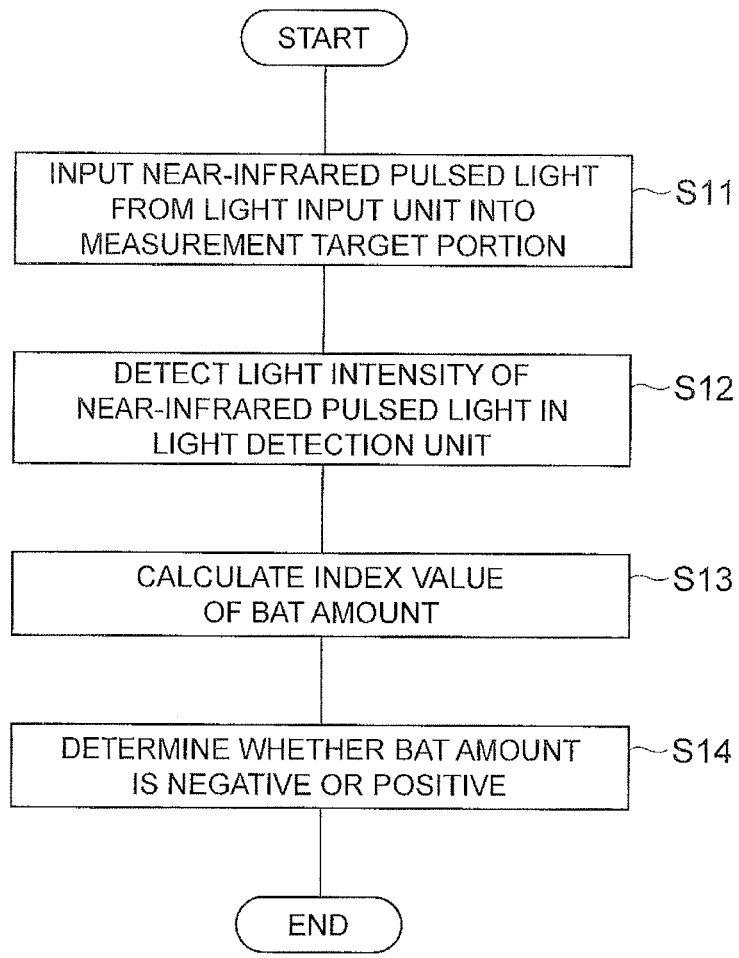
FIG. 42 is a flowchart showing the operation of the measurement apparatus and the measurement method according to the third embodiment.

FIG. 42 is a flowchart showing the operation of the measurement apparatus 1C and the measurement method according to the present embodiment. As shown in FIG. 42, the present embodiment has a determination step S14, in addition to the measurement method in the first embodiment (cf. FIG. 4). In the determination step S14, the determination unit 34 compares the index value for the BAT amount calculated in the calculation step S13 with the predetermined threshold value, thereby determining whether the BAT amount of the subject is negative or positive.

The measurement apparatus 1C and measurement method of the present embodiment can markedly reduce the burden on the subject and can perform the measurement of BAT extremely simply as in the first embodiment. It is believed that the boundary between negativity and positivity of BAT amount is $SUV_{max}$ of about 2.0 and, at present, the determination on whether negative or positive is made by visual inspection of a radiological technologist based on a PET image. Since the BAT amount can be accurately evaluated by the measurement apparatus 1C and measurement method of the present embodiment as described in the foregoing first example, whether the BAT amount is negative or positive can be simply and accurately determined. It is noted that the determination unit 34 in the present embodiment can also be provided in the calculation unit 30B in the second embodiment.

Third Example

In order to examine the effect by the present embodiment, receiver operating characteristic (ROC) curves were created using the determination result by the determination unit 34 (determination step S14) and the determination result by visual inspection based on a PET image. FIG. 43 to FIG. 46 show the results of the examination. (a) in FIG. 43 is the ROC curve of the determination result based on the index value calculated from the oxygenated hemoglobin concentration $C_{HbO2}$. (b) in FIG. 43 is the ROC curve based on the index value calculated from the total hemoglobin concentration $C_{tHb}$, (a) in FIG. 44 that from the absorption coefficient $\mu_a$ (wavelength of 760 nm), (b) in FIG. 44 that from the absorption coefficient $\mu_a$ (wavelength of 800 nm), (a) in FIG. 45 that from the scattering coefficient $\mu'_s$ (wavelength of 760 nm), (b) in FIG. 45 that from the scattering coefficient $\mu'_s$ (wavelength of 800 nm), and (a) in FIG. 46 that from the deoxygenated hemoglobin concentration $C_{Hb}$.

For comparison's sake, (b) in FIG. 46 shows the ROC curve of the determination result based on the index value calculated from the oxygen saturation $SO_2$. In FIG. 43 to FIG. 46, the vertical axis represents positive rate (also referred to as sensitivity or positive predictive value) and the horizontal axis false negative rate (value obtained by subtracting specificity (also referred to as negative predictive value) from 1). In any one of the ROC curves, the correction using the parameter for the body fat amount is not made.

The threshold value (cutoff point), sensitivity (positive predictive value), specificity (negative predictive value), and accuracy (proper diagnosis rate) of each of the ROC curves G21-G28 shown in FIG. 43 to FIG. 46 are those provided in Table 2 below.

TABLE 2

| ROC curve | threshold value (cutoff point) | sensitivity (positive predictive value) | specificity (negative predictive value) | accuracy (proper diagnosis rate) |
|---|---|---|---|---|
| G21 | $C_{HbO2}$: 57-59 μM | 100% | 100% | 100% |
| G22 | $C_{tHb}$: 75 μM | 100% | 94.4% | 96.7% |
| G23 | $\mu_a$: 0.17-0.18 cm$^{-1}$ | 91.7% | 94.4% | 93.3% |
| G24 | $\mu_a$: 0.17-0.18 cm$^{-1}$ | 91.7% | 94.4% | 93.3% |
| G25 | $\mu'_s$: 6.5-7 cm$^{-1}$ | 100% | 88.9% | 93.3% |
| G26 | $\mu'_s$: 6.5-7 cm$^{-1}$ | 100% | 88.9% | 93.3% |
| G27 | $C_{Hb}$: 19.5 μM | 91.7% | 83.3% | 86.7% |
| G28 | $SO_2$: 74% | 50% | 55.6% | 53.3% |

As shown in Table 2, the determination result obtained with the use of the index value calculated from the oxygenated hemoglobin concentration $C_{HbO2}$, the total hemoglobin concentration $C_{tHb}$, the absorption coefficient $\mu_a$, the scattering coefficient $\mu'_s$, or the deoxygenated hemoglobin concentration. $C_{Hb}$ agreed with the determination result by the visual inspection based on the PET image, with high probability. It is seen from this result that the above third embodiment can accurately determine whether the BAT amount is negative or positive.

The measurement method and the measurement apparatus for BAT according to the present invention do not have to be limited to the above-described embodiments, but can be modified in various ways. For example, the hemoglobin concentration is calculated by use of the time-resolved spectroscopy in the above embodiments, but various methods, for example, such as phase modulation spectroscopy, spatially-resolved spectroscopy, and Micro-beer lambert method can be applied to the near-infrared spectroscopy used in the calculation unit and calculation step of the present invention.

A measurement method for brown adipose tissue according to the above embodiment is configured to include a light input step of inputting near-infrared light from a light input unit into a measurement target portion; a light detection step of detecting light intensity of the near-infrared light having propagated through an interior of the measurement target portion by a light detection unit; and a calculation step of calculating an index value for a BAT amount from at least one value of an oxygenated hemoglobin concentration, a total hemoglobin concentration, and a first parameter of the measurement target portion, the first parameter increasing or decreasing depending upon the oxygenated hemoglobin concentration or the total hemoglobin concentration, which are acquired by near-infrared spectroscopy based on the detection result by the light detection unit.

Another measurement method for brown adipose tissue according to the above embodiment is configured to include a light input step of inputting near-infrared light from a light input unit into a measurement target portion; a light detection step of detecting light intensity of the near-infrared light having propagated through an interior of the measurement target portion by a light detection unit; and a calculation step of calculating an index value for a brown adipose tissue amount from at least one of a scattering coefficient and a deoxygenated hemoglobin concentration of the measurement target portion, which are acquired by near-infrared spectroscopy based on the detection result by the light detection unit.

A measurement apparatus for brown adipose tissue according to the above embodiment is configured to include a light input unit for inputting near-infrared light into a measurement target portion; a light detection unit for detecting light intensity of the near-infrared light having propagated through an interior of the measurement target portion; and a calculation unit for calculating an index value for a BAT amount from at least one value of an oxygenated hemoglobin concentration, a total hemoglobin concentration, and a first parameter of the measurement target portion, the first parameter increasing or decreasing depending upon the oxygenated hemoglobin concentration or the total hemoglobin concentration, which are acquired by near-infrared spectroscopy based on the detection result by the light detection unit.

Another measurement apparatus for brown adipose tissue according to the above embodiment is configured to include a light input unit for inputting near-infrared light into a measurement target portion; a light detection unit for detecting light intensity of the near-infrared light having propagated through an interior of the measurement target portion; and a calculation unit for calculating an index value for a brown adipose tissue amount from at least one of a scattering coefficient and a deoxygenated hemoglobin concentration of the measurement target portion, which are acquired by near-infrared spectroscopy based on the detection result by the light detection unit.

The measurement method for brown adipose tissue may be configured so that the calculation step includes defining as the index value for the brown adipose tissue amount, a value corrected so as to reduce influence of a body fat amount included in the at least one value, using data indicating a correlation of a second parameter for the body fat amount with the at least one value or with measurement sensitivity. Similarly, the measurement apparatus for brown adipose tissue may be configured to further include a storage unit storing data indicating a correlation of a second parameter for a body fat amount with the at least one value or with measurement sensitivity, and configured so that the calculation unit defines as the index value for the BAT amount, a value corrected so as to reduce influence of the body fat amount included in the at least one value, using the data.

The hemoglobin concentration measured by the near-infrared spectroscopy is likely to be affected by WAT. Since WAT has the absorbance extremely lower than that of muscle and since the WAT amount or body fat amount significantly differs among individuals, the hemoglobin concentration tends to be estimated lower for people with more body fat and to be estimated higher for people with less body fat. Furthermore, since BAT promotes energy expenditure, the body fat tends to decrease in people with higher activity values of BAT. Since the foregoing method and apparatus define as the index value for the BAT amount the value corrected so as to reduce the influence of the body fat amount included in the hemoglobin concentration or the like, using the data indicating the correlation of the parameter for the body fat amount with the hemoglobin concentration or the like or with the measurement sensitivity, they can more accurately evaluate the BAT amount.

The measurement method for brown adipose tissue may be configured to further include a determination step of comparing the index value with a threshold value to determine whether the brown adipose tissue amount is negative or positive. Similarly, the measurement apparatus for brown adipose tissue may be configured so that the calculation unit compares the index value with a threshold value to determine whether the brown adipose tissue amount is negative or positive. The foregoing measurement method and measurement apparatus for brown adipose tissue can simply and accurately determine whether the BAT amount is negative or positive, because of their high evaluation accuracy.

INDUSTRIAL APPLICABILITY

The present invention is applicable as the measurement method and the measurement apparatus for brown adipose tissue capable of reducing the burden on the subject.

REFERENCE SIGNS LIST

1A—measurement apparatus, 10—light input unit, 11—pulsed light source, 12—light guide for light input, 20—light detection unit, 21—light guide for light detection, 22—photodetector, 30—calculation unit, 31—temporal waveform measurement unit, 32—biological optical characteristic measurement unit, 33—calculation processing unit, 33a—hemoglobin concentration calculation unit, 33b—index value calculation unit, 40—storage unit, 50—parameter input unit, 60—control unit, 70—main body section, 80—display device, B—measurement target portion, D—light detection position, L1—approximate straight line, P(n)—near-infrared pulsed light, S—light input position.

The invention claimed is:

1. A measurement method for brown adipose tissue, comprising:
a light input step of inputting near-infrared light from a light input unit into a measurement target portion;
a light detection step of detecting light intensity of the near-infrared light having propagated through an interior of the measurement target portion by a light detection unit;
a calculation step of measuring any one value of an oxygenated hemoglobin concentration, a total hemoglobin concentration, and a first parameter of the measurement target portion, the first parameter increasing or decreasing depending upon the oxygenated hemoglobin concentration or the total hemoglobin concentration, which are acquired by near-infrared spectroscopy based on the detection result by the light detection unit;
a defining step in which an index value for a brown adipose tissue amount is defined as the any one value measured; and
a determination step of comparing the index value with a threshold value to determine whether the brown adipose tissue amount is negative or positive.

2. The measurement method for brown adipose tissue according to claim 1, wherein the any one value is corrected so as to reduce influence of a body fat amount using data indicating a correlation of a second parameter for the body fat amount with the any one value or with measurement sensitivity.

3. A measurement method for brown adipose tissue, comprising:
a light input step of inputting near-infrared light from a light input unit into a measurement target portion;
a light detection step of detecting light intensity of the near-infrared light having propagated through an interior of the measurement target portion by a light detection unit;
a calculation step of measuring any one value of a scattering coefficient and a deoxygenated hemoglobin concentration of the measurement target portion, which are acquired by near-infrared spectroscopy based on the detection result by the light detection unit;
a defining step in which an index value for a brown adipose tissue amount is defined as the any one value measured; and
a determination step of comparing the index value with a threshold value to determine whether the brown adipose tissue amount is negative or positive.

4. A measurement apparatus for brown adipose tissue, comprising:
a light input unit inputting near-infrared light into a measurement target portion;
a light detection unit detecting light intensity of the near-infrared light having propagated through an interior of the measurement target portion; and
a calculator configured to define an index value for a brown adipose tissue amount by any one value of an oxygenated hemoglobin concentration, a total hemoglobin concentration, and a first parameter of the measurement target portion, the first parameter increasing or decreasing depending upon the oxygenated hemoglobin concentration or the total hemoglobin concentration, which are acquired by near-infrared spectroscopy based on the detection result by the light detection unit, wherein the calculator is configured to compare the index value with a threshold value to determine whether the brown adipose tissue amount is negative or positive.

5. The measurement apparatus for brown adipose tissue according to claim 4, further comprising a storage unit storing data indicating a correlation of a second parameter for a body fat amount with the any one value or with measurement sensitivity,
wherein the any one value is corrected so as to reduce influence of the body fat amount using the data.

6. A measurement apparatus for brown adipose tissue, comprising:
a light input unit inputting near-infrared light into a measurement target portion;
a light detection unit detecting light intensity of the near-infrared light having propagated through an interior of the measurement target portion; and
a calculator configured to define an index value for a brown adipose tissue amount by any one of a scattering coefficient and a deoxygenated hemoglobin concentration of the measurement target portion, which are acquired by near-infrared spectroscopy based on the detection result by the light detection unit, wherein the calculator is configured to compare the index value with a threshold value to determine whether the brown adipose tissue amount is negative or positive.

7. The measurement method for brown adipose tissue according to claim 3, further comprising a determination step of comparing the index value with a threshold value to determine whether the brown adipose tissue amount is negative or positive.

* * * * *